United States Patent
Chang et al.

(10) Patent No.: US 12,286,626 B2
(45) Date of Patent: Apr. 29, 2025

(54) MYOCARDIAL ENHANCER RNA AND METHODS OF USE

(71) Applicant: THE TRUSTEES OF INDIANA UNIVERSITY, Bloomington, IN (US)

(72) Inventors: Ching-Pin Chang, Indianapolis, IN (US); Wei Cheng, Indianapolis, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 1053 days.

(21) Appl. No.: 17/283,845

(22) PCT Filed: Oct. 18, 2019

(86) PCT No.: PCT/US2019/056995
§ 371 (c)(1),
(2) Date: Apr. 8, 2021

(87) PCT Pub. No.: WO2020/081972
PCT Pub. Date: Apr. 23, 2020

(65) Prior Publication Data
US 2021/0380977 A1 Dec. 9, 2021

Related U.S. Application Data

(60) Provisional application No. 62/747,732, filed on Oct. 19, 2018.

(51) Int. Cl.
*C12N 15/113* (2010.01)
*C12Q 1/6883* (2018.01)

(52) U.S. Cl.
CPC .......... *C12N 15/113* (2013.01); *C12Q 1/6883* (2013.01); *C12N 2310/14* (2013.01)

(58) Field of Classification Search
CPC .............. C12N 15/113; C12N 2310/14; C12N 2310/20; C12Q 1/6883; C07K 14/4716
See application file for complete search history.

(56) References Cited

U.S. PATENT DOCUMENTS

2005/0214835 A1 9/2005 Bristow et al.
2016/0114004 A1* 4/2016 Chang .................. A61K 9/0019
800/13

FOREIGN PATENT DOCUMENTS

WO WO-2010006215 A1 * 1/2010 .............. A61P 9/00

OTHER PUBLICATIONS

ABSS SEQ ID No. 2 query, retrieved Jan. 15, 2024 (Year: 2024).*
GenomeMYH7 (MYH7 Genomic Data Viewer, https://www.ncbi.nlm.nih.gov/gdv/browser/gene/?id=4625, retrieved Jul. 10, 2024) (Year: 2024).*
GenBank3 (GenBank3, Human chromosome 14 DNA sequence BAC C-2201G16 of library CalTech-D from chromosome 14 of *Homo sapiens* (Human), complete sequence, https://www.ncbi.nlm.nih.gov/nuccore/AL132855, Mar. 14, 2015, retrieved Jul. 8 2024) (Year: 2015).*
GenBankEnhancer (*Homo sapiens* VISTA enhancer hs2330 (LOC110121504) on chromosome 14, https://www.ncbi.nlm.nih.gov/nuccore/1187954797?sat=48&satkey=90014744, revision Apr. 29, 2017, retrieved Jul. 10, 2024). (Year: 2017).*
PCT International Search Report and Written Opinion completed by the ISA/US on Feb. 8, 2020 and issued in connection with PCT/US2019/056995.
GenBank AL132855.4, Human chromosome 14 DNA sequence BAG C-2201G16 of library CalTech-D from chromosome 14 of *Homo sapiens* (Human), complete sequence, Mar. 14, 2015 (Mar. 14, 2015). [Retrieved on Feb. 8, 2020]. Retrieved from the internet <URL: https://www.ncbi.nlm.nih.gov/nuccore/AL132855> entire document.
GenBank AC157212, Mus musculus BAC clone RP23-171A13 from chromosome 14, complete sequence, Apr. 27, 2005 (Apr. 27, 2005). [Retrieved on Feb. 8, 2020]. Retrieved from the Internet <URL: https://www.ncbi.nlm.nih.gov/nuccore/AC157212> entire document.
Qin et al. "Localization of human cardiac beta-myosin heavy chain gene (MYH7) to chromosome 14q12 by in situ hybridization" Cytogenet Cell Genet, 1990, vol. 54, p. 74-76; abstract.

* cited by examiner

*Primary Examiner* — Ekaterina Poliakova-Georgantas
*Assistant Examiner* — John Charles McKillop
(74) *Attorney, Agent, or Firm* — Barnes & Thornburg LLP

(57) ABSTRACT

Disclosed are methods of detecting myocardial enhancer RNA levels in mammalian cardiomyocytes. In a further embodiment, a method of disrupting assembly of an enhancer DNA-Myh6 promoter-Myh7 promoter complex, is provided wherein the method comprises providing enhancer RNA to a cardiomyocyte.

16 Claims, 12 Drawing Sheets
Specification includes a Sequence Listing.

N=6-15 AT EACH TIME POINT

```
                               SEQUENCE LISTING

<160> NUMBER OF SEQ ID NOS: 44

<210> SEQ ID NO 1
<211> LENGTH: 3302
<212> TYPE: RNA
<213> ORGANISM: Mus musculus

<400> SEQUENCE: 1
cagacacuau gagauggacu cgcaggugcg caggugcggg gcucauuggc uccuuccucc      60
ccuucacaga cagaugcaug gaggcagcuu ggagcagagu uugcaguagc ccccuccucu     120 cccaucccu ccaucuuggg cuuucauuga uuggccugac ugucagccuc cagaggucuc      180
agcucucaag auaaaguggg aggucccguaa ggacugggaa acaagccaug cuuagccugg    240
gcucgagccu uugcuugugc uucaggggucu gcgauuuauc cuagaaaaac aauguuugaa    300
gccagaagug cccuagagca gugauuccca accuucccaa agacccuuuc auacacuucc    360
uccugucaug gugaccucca accauaaaau gauuugcguu gcuacuuccu aacuguaauu    420
uugcuacugu uaugaauugu aacacacaua uuuuuggaga uagagguuuu gucaaaggag    480
ucgagaccca caggcugaga accauuucuc gcgaggcuca uccuaucccg ggaugacuuu    540
cucaucucug ggcugggccc uugcuguucu cuaagaacuu gguacaaugu cugaugcugc    600
acauacuugu agcccaacac ugaguguuga aacuuuggaa cagggauuug aaacagauua    660
agucagccaa uagacacaua cacacacaca cacacacaca cacacacaca cacacgcacg    720
cacgcacgcg caggcacaca cagacuuucc ugggguauggg aaaagguaau uagucacccc    780
ccugaucuga ggcucccaag ucacacuugg aagaagggac gucagggucu ggcugcugcu    840
uucuuccugg gaugcuuuuc aggggcugca ggcagauuac cucuggggduc uguggacaga   900 aacagaaagc uggacagacu cccuaagucu gaagagauga gccuuuauaa aaggacugga    960
aacuaaggaa guuggaagag cucauccuuu cuggucaugg agcguggaga gcaggaggu    1020 gugguuggug gguucaggcu uguguuuugu uuuguuuugu uuuguuguuu uuggagagug   1080
ggagagagga gcagagaggc cuuucgcaaa guugcaaggg uggggcuguc auaggcaggc   1140
ccaacugagc ucuaagauag uaucgaacg gggcaagacu guagaaaugc agaugguugc    1200
uguguggcau ggggauggug accuugccca agggcaguac caggggcagag guuuaggcuu   1260
```

```
gugcaagggg cccgugcugg gccccauguc ucugagauua cagucuuagc ugccaagagc    1320
aacucugugg ggguggaaug aaacaaagca aaggcccuuu guggugcuua gguuccuaau    1380
aauagccaug gcugggcucc aggagaugcc gccauagucu ggcccagucu uguucucgg     1440 agguguuccu gugccuugug ccacggcacu gauugcuaga acuguagcuu guuagcccca    1500
ccucagccuc guuaccugu guuugccugg cucgcugug agagaaggca gagagcuggg      1560
gaagaguggg cgcaaaguca gcacaagggu guuaggagg gagacaaagg gcccaagccu     1620
ggaaaaccaa uaucuccagu cccaacugga acagugaugu ccggggagg agaaaaggug     1680 gaacagagga gccaggacug gcuagaccuc gaaaccgagg gcgccaggug uggaaagacu    1740 uguggggacgu aguggaagga aguguaucga ggaagagaag ugggguucaag aaacuugggg  1800 uggggugagg aaccgauggg gguggaguag auaaggcgaa augacagcgu cuccucagcc    1860
acacaacaga gggggguggca cagcucuugg gaaaacuugg gaagggcucu ugaaggccau   1920
ucccgugaga uaacaaugca cuucaaaucc uuuccuaauc uccccuccua uuauuagccc    1980
ugagcccucu ccaccaagag gccacaggcc ccuaggcugu guccuuuccc ccaugcccuu    2040
ggcuagaauu agaugguccu gucugcgaga ucaucugcua agcaaggucg uucuggcuuc    2100
uggguguugu uacuagagaa gccugaggaa agauggugggg aaggggguugg aaggucacug  2160 aacaacccccc agacacacac uguggguugu gaacaccccc ugauacgaag aggguuagaa   2220
gccaaggccu gaguucuccu gucaauaaau aaacacaucu ucaacgugguu cacaguuuug   2280 aguagcagca uaauuguaga aacagagaag cagaagcagc caugcuggag ggugggcag     2340 aggggagggc uccuggcagg ugagcuugcc gaggggucuu cagaggacug gacuuccagg    2400
uuacacagcc ccagcugcug gccagugcug ugagcguucu ggaggggg agggagggag     2460 agagagagag agagagagag agagagagag agagagagag agagagagag agagagagag   2520
agagagagag agaagagaga agaagaaag gagaagaaag agagaaggaa gagagaagag     2580
agacccaaga caguggcuuc uguaucaguc uguggccuaa gcucuagagg acuagauccc    2640
augagauuag acagggagcc uuagacucca cguuauuuau uuauuuauuu uugguugggg   2700
gagggacuug ccgaguuuca cuagaaacaa ccauugucuu uuugcccugu uuucuccuuc    2760
uguguuuucc cugugggccuc ccucuugccu uuagcucauu guuucagga uuauuuaua    2820 guagacagga gcauguauug caugauuuc aucuggagcu cuucugccuc ugacaaaucu    2880
gaagagaaua aguggaugau gaauaaggua ccaaaggcgg ggagcagcug cugucccugu    2940
gacacugcgu gcugcugaca ggacauagau gggauucucu ggaccucacu cagggagagc    3000
auggcagaga gggcacaucc ugccugaguc uccucugugc cuuucccuug aaucucuccc    3060
ucccuccuuc cuucacccccu uuguccuuu uucucaaaau augaaagcaa uacucauuuu    3120
aaagaugagu aaauuuuggg cuggcucagu gguuagagc acucacugcu cuuccagagg    3180
uccugaguuc aauucccagc aaccauaugg uggcucacaa ccaucuguaa ugggaucgga   3240
ugccuccuuc ugguauaucu gaagacagcu acaaugcagu cauauacauu aaauaaauaa   3300
gc                                                                   3302
```

<210> SEQ ID NO 2
<211> LENGTH: 2373
<212> TYPE: RNA
<213> ORGANISM: Homo sapiens

<400> SEQUENCE: 2

```
gugauucugg guuccuaaga auagcuuggc ugugugggg gaggugucug uagccugccu      60
guccuggguc uuguucucag aggguuucga augccuggug uuggcgggc ucauugcuag     120
uugcugggu aguggaggcc gucagcccac cucagccucu guuaccugug cuuguccagc    180
ucagcuuugg gagaaggcuc aaggcccagg gacaguggag gggcagacac ggaguggccc    240
caaggcuguua agggagagaa gacaaaggcc acaagccugg aaaacaaauu ugaugccuga    300
aagugaagac agggagggu ucuggaaggu aggguugag ggacagcagc cagaagaggc      360
cagagcaggg auggacaugu gggaaggacu uguggggacau ggaggagaag cagagagaau    420
aggugcacgc ggaggccaga auguggaaag caaagggaug aggaauggug caggggaggg    480
ggagcaggau ggacggguug acagagaaga gcagauggaa ggagagaaga gaacgaagcg    540
ggaaaggcag ugggcacuuc cacagagauu ggaggggggu ggcaugacuc uuggaagagc    600
uuggaagcaa ggcucucaaa cgccauuccu gugagauaac aaugcaguca aaucccuccc    660
uaaucucccc uccuauuauu agcccagcgu ccucucagag aauaggccac aggucccugg    720
gcucuguccu uuccccaug cccuuggcug gaauuagaca gacgugccug caugcucauc      780
ugcuaaccac ggugugccgga cuucuaggca augucauugg acaagaggau agagagguag    840
ugggaagggg auggaaggguc accggacacc cuccgggac gaggcagcag cuagacacag      900
agaggggga aggggugcac uagagguicuu ugugcucaaa gacuuuucag aucaauagaa     960
uaaauacaca agcaacauga ucacaaguac aaaauaacau gguuaacacg ugcaaaauaa    1020
cuggaaaguc aaacacauag ccaugggau gcaaagagc ugucaugaaa gggcagagca      1080
gagaggggag gguuucuggg gaaggugagc uggaggugg gucuugagag gauggaucuc      1140
gaggaaccac guccacagcu gcuggccaau gcugugggca uuccggagga agaagggaa     1200
ucaaggagac aguggcuucu augcuacuu uucggccca gccucuaggg gcaagguugu      1260
uaaaagcuua auagcagacu ccuggguuu uaagcacacu gguauuuguu gcuauuuauu    1320
uaaaacugcu guuucuuucu ugccagcgu ggccuuuua cguuuccccc uuagccuccc      1380
ucuugccucu aguaucccua aauacuguuu aucauuuga acuuaaaau ggccaaaagu      1440
uaucauacau auuuuauuu ugagcucuuu ugacucugac aaaucgaaac aaaauaaaua    1500
cuugaugaau aaguaccaa agaaagugag cagcugcugu ucuguguucc uaugagggcu    1560
ccaauugcuc uugcaggaug agggacauag augagauucu cuggaucaua ucagggaga     1620
ggguggagga gggugaggu agcuugcuuu cucucucucu uuucuuucu guuccuucuc      1680
ucucucaacu ugcuuuuuc uuccucucuc cuucuuccu uccuucuu ccuucccc         1740
aaauuauaaa aguaaugcuc auuacuuuaa aaauucaaac aauaaaucuu cuauaaggca    1800
aaacaaguga aguuccuuccc gcuguucaca aucccaucccc caagguuaa uagcagagu      1860
guauccugug cuuguccauu uggaaccuuu uauguauaug cauaaaauac auguugggau    1920
uuuuuuuuuu uuuugacaga gucucacucu gucacucagc cuggaaugca gugugugau     1980
cucugcucac ugcaacuucu gccucccagg uucaagcaau ucuugugucu cagccuccc    2040
aguagcuggg auuacaggug cgcaccacca cccaacua auuuuuuagu agagauggg       2100
uuucaccaug uugcccaggc uggucucgaa uccugagcu caggggucu accugccucg      2160
gccucccaaa gugcuggcau acaggcaug agccaccaca cccguggauu aaaaaaaaaa    2220
uagagacaga gucuuucuau guugcccagg ccguuuuga acuccuggac ucaaacaauc    2280
cuccuggcuu ggcucccaa agugcuggaa uuauggggau gagccauuau gcccagccac    2340
augggaauuu uuuucaacug ggauauaaaa aaa                                 2373
```

<210> SEQ ID NO 3
<211> LENGTH: 5550
<212> TYPE: DNA
<213> ORGANISM: Homo sapiens

<400> SEQUENCE: 3

```
tttgagaatg cctagagagt ttgggtaccc accaccagaa agtgggcttg caaacatgag      60
gctcagctgg ctccctcctc atcttcagat atgcacgtag ggagctcaag gcagagctcg     120
atacagccct ggctgtcatc attgggccca ctcactggct ggagaagggt ctcagcctcc     180
tgagttccat cgtataaaga ttaaagtagg gctggagggc agggagtagc cctagcgaat     240
gatctggaaa catatgtagt gctcagcaat tcaatgtctt ctgcttgttt ttgcttcact     300
atttttactt tacgtagaaa gacaatgtcc ctggtgtgaa ggtacaggtg cctttactgg     360
gcccaaccta caactcagcc ccaagagagc ttcctagtct cttagggcag ggcttttgct     420
ggtgctccag gagaatggtg gaatgctgac ccttctggga tgttctgtgc tgtagcagac     480
atttgagact gcagcagcac ttgctgggtg tgcaagccca gcagaacctt aattccactt     540
tagtgcagaa ccttaattcc agtcctttgc tatacatgcc tcaaagttct ccacaagagt     600
tagaaactga gtaagtaggc aacagataca cacattatgc aggttcttcc agccatggga     660
gaaggtggta agtgacctcc ctgggtctga gagtcacaaa gtcagatttg aacagaggg      720
gcctggggag ctggctggtg ctttttctcca gggaaacttt tccagggcag ctagcagtcc     780
cagtgccaga ctgcctcttg ggtccatgaa tcagattgga ggctgagagc tggtcaggct     840
cctggatgtc tgaagggacc agtgcagagg tttagcttcc ctacctgtag caaggaaaga     900
agggccttta tcaaaggtct gggagtttac tagattaaaa cagctgaacc attctaagca     960
ggaagagtgg gaaggaagca agatgggaca gtagttggtt tgctgggagt gaggaaaagt    1020
caggaaaggg gtccatggag aggctggagg aggggcagag ggggagatat gcagagatat    1080
tgcatagtag cggggctggg ggagctgagg tccggctgtg ggaacaaaga cagtggagtg    1140
acgaggctaa gactgcagaa aaggtgcaga gctgtgtgtc tgtgcatggt ggaggagatg    1200
accttgccca agggcagagc cttgtggctc tgagaagcca gggcaggggg cacaggctcc    1260
agcctggtct ccccgtgcct gggccccttg tctctgagat tacagccttg gctgccaaga    1320
gcagctccat gggggtggtg tggaacaaag cgaacggccc ttttgtgatt ctgggttcct    1380
aagaatagct tggctgtgtg tggggaggtg tctgtagcct gcctgtcctg ggtcttgttc    1440
tcagaggtgt tcgaatgcct ggtgttggcg gggctcattg ctagttgctg gggtagtgga    1500
ggccgtcagc ccacctcagc ctctgttacc tgtgcttgtc cagctcagct ttgggagaag    1560
gctcaaggcc cagggacagt ggaggggcag acacggagtg gccccaaggt gttaagggag    1620
agaagacaaa ggccacaagc ctggaaaaca aatttgatgc ctgaaagtga agacagggag    1680
ggttctggga aggtagggt tgaggacag cagccagaag aggccagagc agggatggac    1740
atgtgggaag gacttgtggg acatggagga gaagcagaga gaataggtgc acgcggaggc    1800
cagaatgtgg aaagcaaagg gatgaggaat ggtccagggg aggggagca ggatggacgg     1860
gttgacagag aagagcagat ggaaggagag aagaaacga agcgggaaag gcagtgggca    1920
cttccacaga gattggaggg gggtggcatg actcttggaa gagcttggaa gcaaggctct    1980
caaacgccat tcctgtgaga taacaatgca gtcaaatccc tccctaatct cccctcctat    2040
tattagccca gcgtcctctc agagaatagg ccacaggtcc ctgggctctg tccttttcccc   2100
```

```
catgcccttg gctggaatta gacagacgtg cctgcatggt catctgctaa ccacggtgtc    2160
cggacttcta ggcaatgtca ttggacaaga ggatagagag gtagtgggaa ggggatggaa    2220
ggtcaccgga caccctccgt ggacgaggca gcagctagac acagagaggg gtgaaggggt    2280
gcactagagg tctttgtgct caaagacttt tcagatcaat agaataaata cacaagcaac    2340
atgatcacaa gtacaaaata acatggttaa cacgtgcaaa ataactggaa agtcaaacac    2400
atagccatgg ggatgcaaaa gagctgtcat gaaagggcag agcagagagg ggagggtttc    2460
tggggaaggt gagcttggag gtgggtcttg agaggatgga tctcgaggaa ccacgtccac    2520
agctgctggc caatgctgtg ggcattccgg aggaaagaag ggaatcaagg agacagtggc    2580
ttctatgtct acttttctgg cccagcctct aggggcaagg ttgttaaaag cttaatagca    2640
gactcctggg ttttaagca cactggtatt tgttgctatt tatttaaaac tgctgttttct    2700
ttcttgtcca gcgtggtcct tttacgtttt ccccttagcc tccctcttgc ctctagtatc    2760
cctaaatact gttatcatt tgatactta aaatggccaa aagttatcat acatattttt    2820
attttgagct cttttgactc tgacaaatcg aaacaaaata aatacttgat gaataatgta    2880
ccaaagaaag tgagcagctg ctgttctgtg ttcctatgag ggctccaatt gctcttgcag    2940
gatgagggac atagatgaga ttctctggat catattcagg gagagggtgg aggagggtgg    3000
aggtagcttg ctttctctct ctctttttct ttctgttcct tctctctctc aacttgcttt    3060
tttcttcctc tctccttctt tccttccttt cttttccttttc tcccaaatta taaaagtaat    3120
gctcattact ttaaaaattc aaacaataaa tcttctataa ggcaaaacaa gtgaagtccc    3180
ttccgctgtt cacaatccca tccccaaagg ttaatagtca gagtgtatcc tgtgcttgtc    3240
catttggaac cttttatgta tatgcataaa atacatgttg ggattttttt tttttttttga   3300
cagagtctca ctctgtcact cagcctggaa tgcagtggtg tgatctctgc tcactgcaac    3360
ttctgcctcc caggttcaag caattcttgt gtctcagcct ccccagtagc tgggattaca    3420
ggtgcgcacc accacaccca actaattttt tagtagagat ggggtttcac catgttgccc    3480
aggctggtct cgaattcctg agctcaggtg gtctacctgc ctcggcctcc caaagtgctg    3540
gcattacagg catgagccac cacacccgtg gattaaaaaa aaaatagaga cagagtctt    3600
ctatgttgcc caggccggtt ttgaactcct ggactcaaac aatcctcctg gcttggcctc    3660
ccaaagtgct ggaattattg ggatgagcca ttatgcccag ccacatggga attttttta    3720
actgggatat aaaaaaatga aacatatata ttcaaccagg gaatgctgac ttaaaaaaaa    3780
tgtatgtagt ttttggaagc ttctcaagtc attaatgatt ccaggatccc tcttcaagtg    3840
acacatgtgg acagttacca gagtcttcag aggctatata gtaatcagca ctcaaaagtg    3900
aatcaaagtg aattttgaga aatgaatgaa agaggccaag gaaggataag aaagaggatg    3960
ccaacccctt ttaacttcag cccttctttg ttcctggaca tcctcctctc aggagaggtc    4020
acttggacaa catctgtctg gggtcagaag tgacagtagg tgcatggtag actctcgggt    4080
catgggagat tatcctcatg gcagagtcac ctgtccctgc ttgtgaaaaa gacttttttt    4140
tttttcacaa tggtagcgtt ggcataatga tgcctagtaa ttacttttgc aaggctggtt    4200
ctgaaatgcc acattttca tgctcagaaa aaggtggtca tttatctgg tcgtttttct    4260
gttttgaact ctggaactca tcctgaatgt cacatttgta cctgttcttt gtgtggaagc    4320
tctaaagtgg cctttagcca aaagtcaatc aaaagttttg agcaagatcc taatatagtt    4380
gatgactgat gcagcccttg agctgacagc tggtgtagca tggatggctg gattcctgat    4440
gtgaaagtat gagaccagaa gcaactgaaa cgcccaactc tctactctca ttctgctctg    4500
```

```
tgctgctccc cctcctcccc actgcgggcc ccacacgaag ccaatactaa ttccccagtt    4560
tctgcctttt cagagaccca ctgtgtgccc tgcccaatca agggaaaag gtgggatgga    4620 aaaaaggaaa gaaaaatata agataattat tatggctcct gacagctctg tcagtaggat    4680
aagggcctga gatatggaac catcctctct tgcaaacagg gagcatgcat gtggaggacc    4740
aaaggtggga ggaaggcttg aaatcaagag aatggagggt gagaaaggga agtgcaggga    4800
gtggggtcta cagccccaaa ggtgagcctc aggaaggcct cacctctctg ggcagtgcca    4860
agaatcctgg ggaagaaaat atgaggagtg gcctggctcc cagcccttgt gtcctacttc    4920
ccctctccca tgcctcatta tacctgaagg gccagtcctg ccctgtccc tggatgcatg    4980 tgagaaccca ggaggaggac ctgcatgggc tctggcctac acttggagtc tcagcatcgt    5040
cactcttgct gctgtgccct agttctagaa attcagcttc tatcttgttc ctaagacttg    5100
ggccccaccc tgtgccgcag gccggtaact gagccctggt tccctctgcc agaggccttg    5160
tcttggtaac cctcttcgtc ttcctggccc tgtctacttc tcagggatta gattttcc    5220 ttaagcccca gccaagaagc cagggcact gttcctgct catagaagga gatagcatat    5280
tttgataact aagaacatag attttggagt cagacttagg ttaaaaaatc ctggctctac    5340
cacgaaccag ctatgtgacc tgggtgtgtc atttaccctc tctgagaaaa aacatgcagt    5400
atcatgtgca gtcttatgac ccaaaatata atccatagac tggcagcatc agcatcagtg    5460
ggagtttgtt agaattgcag aacctcaggc cccagcctag atctattgag acattagcat    5520
gttaacaaga acccaaggtg attttgtgca                                      5550

<210> SEQ ID NO 4
<211> LENGTH: 4011
<212> TYPE: DNA
<213> ORGANISM: Mus musculus

<400> SEQUENCE: 4
ccaggagaat attcgggaag ccaaaaagtt catggaacag agaaaccttg cctcagacct      60
atgtggaagg agggaaccaa tcctgacaag ctgtgccctg accccacgt gtgccctgtg     120 acacaagaga tgcacacatc atgcatgggc acacacacat ccaccacaca tgctaaaaat     180
taggaagtga gaaagatata ggagccaaag agaataaggc gagacttgtt tcctagaaat     240
cccagaagtc tttcaagagg agcaggtggc cggtagtgtc agattccaaa gaaaggcaga     300
gtgacaggag aagagagctt gggtggctgt tcaggaagca gcttccagag agtcccaggg     360
cagtgccagg gtgctggggt ttaatcagga ataaggacga gcaggattta agctgagtag     420
atgggagtta aaggaacgga ataggaagtg caggcagcgg gggttccagc ttccaaggca     480
gcgatttggc aacagaatga atgagccagg aagtgggtca gatagcacgg tttattttgt     540
tttttaagat aaggcaaccc tgagcacgtg gagcaggggt gttaaaggat gtccttggtt     600
tgctctctgt ttcctttggg cctctctggc actgttttct tatttccagc tctcttctg     660 gaactcagga gggtggcgag taaatgctca gacactatga gatggactcg caggtgcgca     720 ggtgcgggc tcattggctc cttcctcccc ttcacagaca gatgcatgga ggcagcttgg     780
agcagagttt gcagtagccc cctcctctcc catcccctcc atcttgggct ttcattgatt     840
ggcctgactg tcagcctcca gaggtctcag ctctcaagat aaagtgggag gtccgtaagg     900
actgggaaac aagccatgct tagcctgggc tcgagccttt gcttgtgctt cagggtctgc     960
gatttatcct agaaaaacaa tgtttgaagc cagaagtgcc ctagagcagt gattcccaac    1020
```

-continued

```
cttcccaaag acccttcat acacttcctc ctgtcatggt gacctccaac cataaaatga   1080
tttgcgttgc tacttcctaa ctgtaattt gctactgtta tgaattgtaa cacacatatt    1140
tttggagata gaggttttgt caaggagtc gagacccaca ggctgagaac catttctcgc    1200
gaggctcatc ctatcccggg atgactttct catctctggg ctgggccctt gctgttctct   1260
aagaacttgg tacaatgtct gatgctgcac atacttgtag cccaacactg agtgttgaaa   1320
ctttggaaca gggatttgaa acagattaag tcagccaata gacacataca cacacacaca   1380
cacacacaca cacacacaca cacgcacgca cgcacgcgca ggcacacaca gactttcctg   1440
ggtatgggaa aaggtaatta gtcaccccc tgatctgagg ctcccaagtc acacttggaa    1500
gaagggacgt cagggtctgg ctgctgcttt cttcctggga tgcttttcag gggctgcagg   1560
cagattacct ctgggtctg tggacagaaa cagaaagctg gacagactcc ctaagtctga    1620
agagatgagc ctttataaaa ggactggaaa ctaaggaagt tggaagagct catcctttct   1680
ggtcatggag cgtggagagc aggagggtgt ggttggtggg ttcaggcttg tgtttgttt    1740 tgttttgttt tgttgttttt ggagagtggg agagaggagc agagaggcct tctgcaaagt   1800
tgcaagggtg gggctgtcat aggcaggccc aactgagctc taagatagta tctgaacggg   1860
gcaagactgt agaatgtcag atggttgctg tgtgtcatgg ggatggtgac cttgcccaag   1920
ggcagtacca gggcagaggt ttaggcttgt gcaaggggcc cgtgctgggc cccatgtctc   1980
tgagattaca gtcttagctg ccaagagcaa ctctgtgggg gtggaatgaa acaaagcaaa   2040 ggccctttg tggtgctagg ttcctaataa tagccatggc tgggctccag gagatgccgc    2100
catagtctgg ccccagtctt gttctcggag gtgttcctgt gccttgtgcc acggcactga   2160
ttgctagaac tgtagcttgt tagccccacc tcagcctctg ttacctgtgt ttgcctggct   2220
ctgctgtgag agaaggcaga gagctgggga agagtgggcg caaagtcagc acagggtgt    2280 tagggaggga gacaaagggc ccaagcctgg aaaaccaata tctccagtcc caactggaac   2340
agtgatgttc cggggaggag aaaaggtgga acagaggagc caggactggc tagacctcga   2400
aaccgagggc gccaggtgtg gaaagacttg tgggacgtag tggaaggaag tgtatcgagg   2460
aagagaagtg ggttcaagaa acttggggtg gggtgaggaa ccgatggggg tggagtagat   2520
aaggcgaaat gacagcgtct cctcagccac acaacagagg gggtggcaca gctcttggga   2580
aaacttggga agggctcttg aaggccattc ccgtgagata acaatgcact tcaaatcctt   2640
tcctaatctc ccctcctatt attagccctg agtcctctcc accaagaggc cacaggcccc   2700
taggctgtgt cctttccccc atgcccttgg ctagaattag atggtcctgt ctgcgagatc   2760
atctgctaag caaggtcgtt ctggcttctg ggtgttgtta ctagagaagc ctgtggaaag   2820
atggtgggaa ggggttggaa ggtcactgaa caaccccag acacacactg tggttgtgga    2880
acaccccctg atacgaagag ggttagaagc caaggcctga gttctcctgt caataaataa   2940
acacatcttc aacgtggtca cagttttgag tagcagcata attgtagaaa cagagaagca   3000
gaagcagcca tgctggaggg tggggcagag gggagggctc ctggcaggtg agcttgccga   3060
ggggtcttca gaggactgga cttccaggtt acacagcccc agctgctggc cagtgctgtg   3120
agcgttctgg agggagggag ggagggagag agagagagag agagagagag agagagagag   3180
agagagagag agagagagag agagagagag agagagagag aagagagaag aaagaaagga   3240
gaagaaagag agaaggaaga gagaagagag acccaagaca gtggcttctg tatcagtctg   3300
tggcctaagc tctagaggac tagatcccat gagattagac agggagcctt agactccacg   3360
ttatttattt attatttttt ggttggggga gggacttgcc gagtttcact agaaacaacc   3420
```

```
attgtcttttt tgccctgttt tctccttctg tgttttccct gtggcctccc tcttgccttt    3480
agctcattgt tttcaggatt attttatagt agacaggagc atgtattgca tgtatttcat    3540
ctggagctct tctgcctctg acaaatctga agagaataag tggatgatga ataaggtacc    3600
aaaggcgggg agcagctgct gtccctgtga cactgcgtgc tgctgacagg acatagatgg    3660
gattctctgg acctcactca gggagagcat ggcagagagg gcacatcctg cctgtgtctc    3720
ctctgtgcct ttcccttgaa tctctccctc cctccttcct tcaccccttt gttccttttt    3780
ctcaaaatat gaaagcaata ctcattttaa agatgagtaa attttgggct ggctcagtgg    3840
ttaagagcac tcactgctct tccagaggtc ctgagttcaa ttcccagcaa ccatatggtg    3900
gctcacaacc atctgtaatg ggatcggatg cctccttctg gtatatctga agacagctac    3960
aatgcagtca tatacattaa ataaataagc ctttaaaaag aaaaaagatg a              4011
```

```
<210> SEQ ID NO 5
<211> LENGTH: 3302
<212> TYPE: DNA
<213> ORGANISM: Mus macedonicus

<400> SEQUENCE: 5
cagacactat gagatggact cgcaggtgcg caggtgcggg gctcattggc tccttcctcc      60
ccttcacaga cagatgcatg gaggcagctt ggagcagagt ttgcagtagc cccctcctct     120
cccatcccct ccatcttggg ctttcattga ttggcctgac tgtcagcctc cagaggtctc     180
agctctcaag ataaagtggg aggtccgtaa ggactgggaa acaagccatg cttagcctgg     240
gctcgagcct ttgcttgtgc ttcagggtct gcgatttatc ctagaaaaac aatgtttgaa     300
gccagaagtg ccctagagca gtgattccca accttcccaa agacccttc atacacttcc     360 tcctgtcatg gtgacctcca accataaaat gatttgcgtt gctacttcct aactgtaatt     420
ttgctactgt tatgaattgt aacacacata ttttggaga tagaggtttt gtcaaaggag      480
tcgagaccca caggctgaga accatttctc gcgaggctca tcctatcccg ggatgacttt     540
ctcatctctg ggctgggccc ttgctgttct ctaagaactt ggtacaatgt ctgatgctgc     600
acatacttgt agcccaacac tgagtgttga aactttggaa cagggatttg aaacagatta     660
agtcagccaa tagacacata cacacacaca cacacacaca cacacacaca cacgcacg      720 cacgcacgcg caggcacaca cagactttcc tgggtatggg aaaaggtaat tagtcacccc     780
cctgatctga ggctcccaag tcacacttgg aagaagggac gtcagggtct ggctgctgct     840
ttcttcctgg gatgctttc aggggctgca ggcagattac ctctggggtc tgtggacaga     900
aacagaaagc tggacagact ccctaagtct gaagagatga gcctttataa aaggactgga     960
aactaaggaa gttggaagag ctcatccttt ctggtcatgg agcgtggaga gcaggagggt    1020
gtggttggtg ggttcaggct tgtgttttgt tttgttttgt tttgttgttt ttggagagtg    1080
ggagagagga gcagagaggc cttctgcaaa gttgcaaggg tggggctgtc ataggcaggc    1140
ccaactgagc tctaagatag tatctgaacg gggcaagact gtagaatgtc agatggttgc    1200
tgtgtgtcat ggggatggtg accttgccca agggcagtac cagggcagag gtttaggctt    1260
gtgcaagggg cccgtgctgg gccccatgtc tctgagatta cagtcttagc tgccaagagc    1320
aactctgtgg gggtggaatg aaacaaagca aaggcccttt tgtggtgcta ggttcctaat    1380
aatagccatg gctgggctcc aggagatgcc gccatagtct ggccccagtc ttgttctcgg    1440
aggtgttcct gtgccttgtg ccacggcact gattgctaga actgtagctt gttagcccca    1500
```

```
cctcagcctc tgttacctgt gtttgcctgg ctctgctgtg agagaaggca gagagctggg    1560
gaagagtggg cgcaaagtca gcacaagggt gttagggagg gagacaaagg gcccaagcct    1620
ggaaaaccaa tatctccagt cccaactgga acagtgatgt tccggggagg agaaaaggtg    1680
gaacagagga gccaggactg gctagacctc gaaaccgagg gcgccaggtg tggaaagact    1740
tgtgggacgt agtggaagga agtgtatcga ggaagagaag tgggttcaag aaacttgggg    1800
tggggtgagg aaccgatggg ggtggagtag ataaggcgaa atgacagcgt ctcctcagcc    1860
acacaacaga gggggtggca cagctcttgg gaaaacttgg gaagggctct tgaaggccat    1920
tcccgtgaga taacaatgca cttcaaatcc tttcctaatc tcccctccta ttattagccc    1980
tgagtcctct ccaccaagag gccacaggcc cctaggctgt gtcctttccc ccatgccctt    2040
ggctagaatt agatggtcct gtctgcgaga tcatctgcta agcaaggtcg ttctggcttc    2100
tgggtgttgt tactagagaa gcctgtgaaa agatggtggg aaggggttgg aaggtcactg    2160 aacaacccccc agacacacac tgtggttgtg aacacccccc tgatacgaag agggttagaa    2220
gccaaggcct gagttctcct gtcaataaat aaacacatct tcaacgtggt cacagttttg    2280
agtagcagca taattgtaga aacagagaag cagaagcagc catgctggag ggtggggcag    2340
aggggagggc tcctggcagg tgagcttgcc gaggggtctt cagaggactg gacttccagg    2400
ttacacagcc ccagctgctg gccagtgctg tgagcgttct ggagggaggg agggagggag    2460
agagagagag agagagagag agagagagag agagagagag agagagagag agagagagag    2520
agagagagag agaagagaga agaaagaaag gagaagaaag agagaaggaa gagagaagag    2580
agacccaaga cagtggcttc tgtatcagtc tgtggcctaa gctctagagg actagatccc    2640
atgagattag acagggagcc ttagactcca cgttatttat ttatttattt ttggttgggg    2700
gagggacttg ccgagtttca ctagaaacaa ccattgtctt tttgccctgt tttctccttc    2760
tgtgttttcc ctgtggcctc cctcttgcct ttagctcatt gttttcagga ttattttata    2820
gtagacagga gcatgtattg catgtattc atctggagct cttctgcctc tgacaaatct    2880
gaagagaata agtggatgat gaataaggta ccaaaggcgg ggagcagctg ctgtccctgt    2940
gacactgcgt gctgctgaca ggacatagat gggattctct ggacctcact cagggagagc    3000
atggcagaga gggcacatcc tgcctgtgtc tcctctgtgc cttttccttg aatctctccc    3060
tccctccttc cttcaccctt tgttcctttt ttctcaaaat atgaaagcaa tactcatttt    3120
aaagatgagt aaattttggg ctggctcagt ggttaagagc actcactgct cttccagagg    3180
tcctgagttc aattcccagc aaccatatgg tggctcacaa ccatctgtaa tgggatcgga    3240
tgcctccttc tggtatatct gaagacagct acaatgcagt catatacatt aaataaataa    3300
gc                                                                  3302
```

<210> SEQ ID NO 6
<211> LENGTH: 2373
<212> TYPE: DNA
<213> ORGANISM: Homo sapiens
<400> SEQUENCE: 6

```
gtgattctgg gttcctaaga atagcttggc tgtgtgtggg gaggtgtctg tagcctgcct      60
gtcctgggtc ttgttctcag aggtgttcga atgcctggtg ttggcggggc tcattgctag     120
ttgctggggt agtggaggcc gtcagcccac ctcagcctct gttacctgtg cttgtccagc     180
tcagctttgg gagaaggctc aaggcccagg gacagtggag gggcagacac ggagtggccc     240
caaggtgtta agggagagaa gacaaaggcc acaagcctgg aaaacaaatt tgatgcctga     300
```

```
aagtgaagac agggagggtt ctgggaaggt aggggttgag ggacagcagc cagaagaggc    360
cagagcaggg atggacatgt gggaaggact tgtgggacat ggaggagaag cagagagaat    420
aggtgcacgc ggaggccaga atgtggaaag caaagggatg aggaatggtc caggggaggg    480
ggagcaggat ggacgggttg acagagaaga gcagatggaa ggagagaaga gaacgaagcg    540
ggaaaggcag tgggcacttc cacagagatt ggaggggggt ggcatgactc ttggaagagc    600
ttggaagcaa ggctctcaaa cgccattcct gtgagataac aatgcagtca aatccctccc    660
taatctcccc tcctattatt agcccagcgt cctctcagag aataggccac aggtccctgg    720
gctctgtcct ttcccccatg cccttggctg gaattagaca gacgtgcctg catggtcatc    780
tgctaaccac ggtgtccgga cttctaggca atgtcattgg acaagaggat agagaggtag    840
tgggaagggg atggaaggtc accggacacc ctccgtggac gaggcagcag ctagacacag    900
agaggggtga agggtgcac tagaggtctt tgtgctcaaa gacttttcag atcaatagaa    960
taaatacaca agcaacatga tcacaagtac aaaataacat ggttaacacg tgcaaaataa   1020
ctggaaagtc aaacacatag ccatggggat gcaaagagc tgtcatgaaa gggcagagca   1080
gagaggggag ggtttctggg gaaggtgagc ttggaggtgg gtcttgagag gatggatctc   1140
gaggaaccac gtccacagct gctggccaat gctgtgggca ttccggagga aagaagggaa   1200
tcaaggagac agtggcttct atgtctactt ttctggccca gcctctaggg gcaaggttgt   1260
taaaagctta atagcagact cctgggtttt taagcacact ggtatttgtt gctatttatt   1320
taaaactgct gtttctttct tgtccagcgt ggtccttta cgttttcccc ttagcctccc   1380
tcttgcctct agtatcccta aatactgttt atcattttga tacttaaaat ggccaaaagt   1440
tatcatacat attttatt tgagctcttt tgactctgac aaatcgaaac aaaataaata   1500
cttgatgaat aatgtaccaa agaaagtgag cagctgctgt tctgtgttcc tatgagggct   1560
ccaattgctc ttgcaggatg agggacatag atgagattct ctggatcata ttcagggaga   1620
gggtggagga gggtggaggt agcttgcttt ctctctctct tttcttctt gttccttctc   1680 tctctcaact tgcttttttc ttcctctctc cttctttcct tcctttctt cctttctccc   1740 aaattataaa agtaatgctc attactttaa aaattcaaac aataaatctt ctataaggca   1800
aaacaagtga agtcccttcc gctgttcaca atcccatccc caaaggttaa tagtcagagt   1860
gtatcctgtg cttgtccatt tggaacctt tatgtatatg cataaaatac atgttgggat   1920 ttttttttt ttttgacaga gtctcactct gtcactcagc ctggaatgca gtggtgtgat   1980
ctctgctcac tgcaacttct gcctcccagg ttcaagcaat tcttgtgtct cagcctcccc   2040
agtagctggg attacaggtg cgcaccacca cacccaacta attttttagt agagatgggg   2100
tttcaccatg ttgcccaggc tggtctcgaa ttcctgagct caggtggtct acctgcctcg   2160
gcctcccaaa gtgctggcat tacaggcatg agccaccaca cccgtggatt aaaaaaaaaa   2220
tagagacaga gtcttctat gttgcccagg ccggttttga actcctggac tcaaacaatc   2280
ctcctggctt ggcctcccaa agtgctggaa ttattgggat gagccattat gcccagccac   2340
atgggaattt ttttcaactg ggatataaaa aaa                                2373
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caaccctgag cacgtggagc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggcttaagag atcctcttgg                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acactatgag atggactcgc                                               20

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taatacgact cactatagcc ttgtcttccc                                    30

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tattaaccct cactaaaggg aagcccaga                                     29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taatacgact cactatagcc gctcttgag                                     29

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tattaaccct cactaaaggg acctaaacct c    31

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taatacgact cactatagcc cttgaggg    28

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tattaaccct cactaaaggg aatgggctg    29

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cttcgtatca gggggtgttc c    21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17 gaagggggttg gaaggtcact    20

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcctaggggc ctgtggcctc ttgg    24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccaagaggcc acaggcccct aggc                                           24

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tacctctcta tcctcttgtc caatgacatt gcc                                 33

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggaggggggt ggcatgactc ttggaaga                                       28

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaggcatccg atcccattac aga                                            23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cttcccacta cctctctatc                                                20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctctgtggcg gcagcagcta ttt                                            23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgagggtaga tcagtctgta gga                                                 23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acggtgacca taaaggagga                                                     20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgtcctcgat cttgtcgaac                                                     20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 gcccttttgac ctcaagaaag                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cttcacagtc accgtcttgc                                                     20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcagtctgtg gcctaagctc                                                     20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaactcggc aagtccctc                                                      19

```
<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gagcagttct gatcgggcaa                                               20

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgagggtaga tcagtctgta gga                                           23

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttcaggattc tccgtgaagg g                                             21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtcgaacttg ggtgggttct                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gagctcacct accagacgga                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctcattcaa gcccttcgtg                                               20
```

```
<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agtggcccca aggtgttaag                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgcgtgcacc tattctctct                                                    20

<210> SEQ ID NO 40
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttaatacgac tcactatagg tcagccacac aacagagggg gtggcacagc tcttggga          58

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggtcagccac acaacagagg gggtggcaca gctcttggga                              40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggtcagccac acaacagaaa aaatggcaca gctcttggga                              40

<210> SEQ ID NO 43
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide -binding motif

<400> SEQUENCE: 43 aggggggtgg                                                                9
```

```
<210> SEQ ID NO 44
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 aaaaaatgg                                                                 9
```

MYOCARDIAL ENHANCER RNA AND METHODS OF USE

CROSS REFERENCE TO RELATED APPLICATIONS

This application is a U.S. national counterpart application of international application serial No. PCT/US2019/056995 filed Oct. 18, 2019, which claims priority to U.S. Provisional Patent Application No. 62/747,732 filed on Oct. 19, 2018. The disclosures of both of which are hereby expressly incorporated by reference in their entireties.

STATEMENT OF GOVERNMENT SUPPORT

This invention was made with government support under HL118087 and HL121197 awarded by the National Institutes of Health. The Government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 36 kilobytes ACII (Text) file named "299852_ST25.txt," created on Oct. 15, 2019.

BACKGROUND OF THE DISCLOSURE

Many transcriptional circuits are controlled by enhancer-promoter interactions. An enhancer is a relatively short (50-1500 bp) region of DNA that can be bound by proteins (activators) to increase the likelihood that transcription of a particular gene will occur. Enhancers are cis-acting and can be located up to 1 Mbp (1,000,000 bp) upstream or downstream from the transcription start site of the gene they regulate. In eukaryotic cells the chromatin complex of DNA is folded so although the enhancer DNA may be far from the gene in a linear way, it is spatially close to the promoter and gene. This allows it to interact with the general transcription factors and RNA polymerase II required for expression of the gene. Many active enhancers transcribe noncoding, enhancer RNAs (eRNAs), capable of facilitating enhancer-promoter interactions for gene regulation, and levels of eRNAs reflect the degree of enhancer and promoter activation.

SUMMARY

The present disclosure relates generally to the use of noncoding enhancer RNAs (eRNAs) as therapeutic agents. More specifically, the present disclosure relates to the use of noncoding myocardial eRNAs to inhibit the formation of a transcriptional complex between the myocardial enhancer DNA (eDNA) and the promoters of the myocardial myosin heavy chain genes (Myh6 and Myh7) in a cardiomyocyte (the eDNA-Myh6 promoter-Myh7 promoter complex). In one embodiment the nonencoding eRNA is a cardioprotective eRNA, named Uheart (Uhrt) for Upstream Myosin Heavy chain RNA Transcript, optionally wherein the Uhrt is an RNA comprising a sequence having at least 95% sequence identity to SEQ ID NO: 1 or SEQ ID NO: 2. A representative listing of relevant sequence identifiers is as follows:

SEQ ID NO: 1 is mouse Uhrt RNA
SEQ ID NO: 2 is human Uhrt RNA
SEQ ID NO: 3 is human enhancer DNA
SEQ ID NO: 4 is mouse enhancer DNA
SEQ ID NO: 5 is mouse Uhrt DNA equivalent
SEQ ID NO: 6 is human Uhrt DNA equivalent In one embodiment, a method of inhibiting the assembly of an enhancer DNA-Myh6 promoter-Myh7 promoter complex is provided. In some embodiments, the method comprises enhancing the percentage of myocardial enhancer DNA that is bound to Uhrt. In some embodiments, the enhancer DNA comprises a sequence selected from the group of SEQ ID NO: 3 and sequences having at least 95% sequence identity with SEQ ID NO: 3. In one embodiment the method comprises increasing the intracellular concentration of active Uhrt RNA and/or increasing the percentage of myocardial eDNA that has an Uhrt RNA bound to it.

In accordance with one embodiment an isolated nucleic acid comprising a sequence having at least 95% sequence identity to SEQ ID NO: 1 or SEQ ID NO: 2 is provided, or a cDNA derivative of such sequences. In one embodiment the isolated nucleic acid comprises a sequence selected from the group consisting of SEQ ID NO: 1, a cDNA complement of SEQ ID NO: 1, SEQ ID NO: 2, and a cDNA complement of SEQ ID NO:2. In one embodiment a nucleic acid is provided comprising a sequence having at least 95% sequence identity to SEQ ID NO:1, a cDNA complement of SEQ ID NO: 1, SEQ ID NO:2, or a cDNA complement of SEQ ID NO: 2, wherein the nucleic acids are modified to comprise a covalently linked detectable marker. In some embodiments, a nucleic acid sequence is provided comprising SEQ ID NO: 1 coupled to a detectable marker. In some embodiments, a nucleic acid sequence is provided comprising SEQ ID NO: 2 coupled to a detectable marker.

In some embodiments, a method of measuring Uhrt in a patient biological sample is provided. In one embodiment, the method comprises providing an RNA sample recovered from the patient and conducting quantitative reverse transcriptase polymerase chain reaction (rtPCR) using primers that specifically bind to Uhrt cDNA, and detecting the detecting the resulting amplicon as a measure of the Uhrt in the patient sample.

In some embodiments, a method of identifying a patient at risk for hypertrophy is provided. In one embodiment, the method comprises providing a sample of RNA recovered from cardiomyocytes from the patient, analyzing the levels of Uhrt RNA, and comparing the Uhrt RNA levels in the patient cardiomyocytes to a reference sample. In one illustrative embodiment, if the analysis of the relative concentration of patient Uhrt RNA is lower than the reference sample Uhrt RNA level, then the patient is identified as at risk for hypertrophy. In one embodiment the reference sample is an RNA sample recovered from myocardial cells of one or more healthy individuals that are free of any cardiac disease.

In some embodiments, a method of treating a patient for heart disease is provided. In some embodiment, the method comprises administering an RNA sequence to the patient. In some embodiments the RNA sequence comprises a sequence having at least 95% sequence identity to SEQ ID NO: 2 or its corresponding DNA equivalent thereof.

In some embodiments, a method of switching a cardiomyocyte from a stressed-state to a non-stressed state is provided. In some embodiments, the method comprises decreasing Brg1 activity and increasing Uhrt activity.

In some embodiments, a method of detecting a patient at risk for hypertrophy is provided. The method comprises providing a test sample comprising RNA from the patient, contacting the test sample with a reverse transcriptase primer specific for an enhancer RNA comprising the sequence for Uhrt, reverse transcribing the enhancer RNA to produce a corresponding test cDNA, contacting the test cDNA with PCR primers specific for Uhrt RNA, conducting a PCR reaction on the test cDNA, detecting the amplified product, determining the concentration of the enhancer RNA in the test sample, and obtaining a reference concentration of the corresponding enhancer RNA. In some embodiments, if the enhancer RNA in the test sample is lower in concentration or level than the reference concentration level, then the patient is at risk or may be diagnosed with hypertrophy. In one embodiment the reference sample represents the average concentration of an eRNA having at least 95% sequence identity to SEQ ID NO: 2 as found in the general population.

DETAILED DESCRIPTION

Definitions

Figure 1:
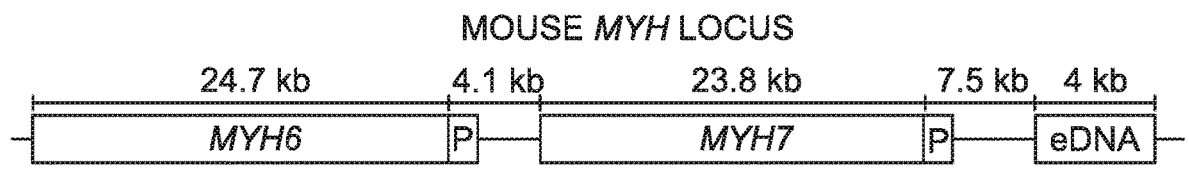
FIG. 1 is an illustration depicting a mouse Myh locus, showing the size of Myh6, Myh7, and eDNA.

In describing and claiming the invention, the following terminology will be used in accordance with the definitions set forth below.

As used herein, the term "Uhrt" includes any RNA sequence that binds to an enhancer DNA (eDNA) that participates in an enhancer DNA-Myh6 promoter-Myh7 promoter complex in a mammalian cardiomyocyte. For example this includes both the mouse Uhrt and human Uhrt of SEQ ID NOs: 1 and 2, respectively. In some embodiments human Uhrt is denoted as UHRT.

As used herein, the term "enhancer" refers to a region of DNA that can increase the likelihood that a cis linked gene is transcribed. A myocardial eDNA is an enhancer element located in a patient's cardiomyocyte that helps regulate the expression of Myh7 and Myh6.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of an enhancer RNA, an interference RNA, or antisense RNA mimetic refers to a nontoxic but sufficient amount of the compound to provide the desired effect. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein the term "isolated" describes a polynucleotide, a polypeptide, or a cell that is in an environment different from that in which the polynucleotide, the polypeptide, or the cell naturally occurs.

As used herein the term "detectable marker" describes a molecule conjugated directly or indirectly to a second molecule to facilitate detection of the second molecule. Specific, non-limiting examples of labels include fluorescent tags, enzymatic linkages, and radioactive isotopes.

As used herein, "a reference sample" refers to a sample that is representative of the general population. A test sample is the sample to be analyzed. The reference sample is distinguished from individuals or a subpopulation that displays or expresses a genotypic or phenotypic characteristic that is not present in the majority of a relevant population as a whole. The reference sample may be based on population data (i.e., average concentration of a molecule) or may be a sample recovered from an individual or from a control population know to lack the genotypic or phenotypic characteristic not present in the majority of the relevant population as a whole.

As used herein, "a reference concentration" refers to the concentration of a molecule in the reference sample As used herein, "Uhrt activity" refers to the ability of a Uhrt nucleic acid to specifically bind to its corresponding eDNA.

As used herein, "Brg1 activity" refers to the ability of a Brg1 protein to specifically bind to the eDNA-Myh6 promoter-Myh7 promoter complex.

As used herein the term "patient" without further designation is intended to encompass any warm blooded vertebrate domesticated animal (including for example, but not limited to livestock, horses, mice, cats, dogs and other pets) and humans.

Embodiments

In one embodiment, the present disclosure is directed to the use of noncoding RNAs to inhibit the assembly of an enhancer DNA-Myh6 promoter-Myh7 promoter complex. In some embodiments, a method of inhibiting assembly of an enhancer DNA-Myh6 promoter-Myh7 promoter complex in a cell is a provided. In some embodiments, the cell is a heart cell. In some embodiments, the cell is a cardiomyocyte.

In some embodiments, a method of inhibiting assembly of an enhancer DNA-Myh6 promoter-Myh7 promoter complex in a cardiomyocyte comprising enhancing binding of Uhrt to the enhancer DNA is provided. In some embodiments, the enhancer DNA comprises a sequence selected from the group consisting of SEQ ID NO: 3, SEQ ID NO: 4, sequences having at least 95% sequence identity to SEQ ID NO: 3 and sequences having at least 95% sequence identity to SEQ ID NO: 4, and the Uhrt is an RNA sequence selected from the group consisting of SEQ ID NO: 1, SEQ ID NO: 2, sequences having at least 95% sequence identity to SEQ ID NO: 1 and sequences having at least 95% sequence identity to SEQ ID NO: 2 or a DNA equivalent of said RNA sequences.

In one embodiment, the method comprises increasing the intracellular concentration of active Uhrt RNA and/or increasing the percentage of myocardial eDNA that is bound to Uhrt RNA. In some embodiments, increasing the intracellular concentration of active Uhrt RNA comprises introducing additional Uhrt RNA into a cardiomyocyte. In an alternative embodiment, a cDNA equivalent of Uhrt may be provided intracellularly to the cardiomyocyte. An active Uhrt RNA or its cDNA equivalent refers to an isolated nucleic acid that is able to bind to eDNA.

In some embodiments, the enhancer DNA comprises a sequence having at least 90%, 91%, 92%, 93%, 94%, 95%, 96%, 97%, 98%, or 99% sequence identity to SEQ ID NO: 3. In some embodiments, the enhancer DNA consists essentially of a sequence having at least 90%, 91%, 92%, 93%, 94%, 95%, 96%, 97%, 98%, or 99% sequence identity to SEQ ID NO: 4. In some embodiments, the enhancer DNA consists of a sequence having at least 95% sequence identity to SEQ ID NO: 3. In some embodiments, the enhancer DNA consists of SEQ ID NO: 3.

In some embodiments, a method of inhibiting assembly of an eDNA-Myh6 promoter-Myh7 promoter complex in a cardiomyocyte is provided. The method comprises enhancing binding of Uhrt to said enhancer. In some embodiments, the Uhrt comprises an RNA sequence having at least 95% sequence identity to SEQ ID NO: 2 or its cDNA equivalent thereof. In some embodiments, the Uhrt comprises an RNA sequence having at least 90%, 91%, 92%, 93%, 94%, 95%, 96%, 97%, 98%, or 99% sequence identity to SEQ ID NO: 2 or its cDNA equivalent thereof. In some embodiments, the Uhrt RNA comprises SEQ ID NO: 2 or its cDNA equivalent thereof. In some embodiments, the enhancer DNA comprises SEQ ID NO: 3 and the Uhrt comprises SEQ ID NO: 2 or its cDNA equivalent.

In some embodiments, the method of inhibiting assembly of an eDNA-Myh6 promoter-Myh7 promoter complex in a cardiomyocyte comprises a step of increasing the amount of Uhrt binding to said enhancer. In some embodiments, the Uhrt comprises an RNA sequence having at least 95% sequence identity to SEQ ID NO: 1 or its cDNA equivalent thereof. In some embodiments, the Uhrt comprises an RNA sequence having at least 90%, 91%, 92%, 93%, 94%, 95%, 96%, 97%, 98%, or 99% sequence identity to SEQ ID NO: 1 or its cDNA equivalent thereof. In some embodiments, the Uhrt RNA comprises SEQ ID NO: 2 or its cDNA equivalent thereof. In some embodiments, the enhancer DNA comprises SEQ ID NO: 3 and the Uhrt comprises SEQ ID NO:1 or its cDNA equivalent. In some embodiments, the enhancer DNA comprises SEQ ID NO: 4 and the Uhrt comprises SEQ ID NO: 1 or its cDNA equivalent. In one embodiment the enhancer DNA comprises SEQ ID NO: 3 and the Uhrt comprises SEQ ID NO: 2 or its cDNA equivalent.

In some embodiments, the method of inhibiting assembly of an eDNA-Myh6 promoter-Myh7 promoter complex in a cardiomyocyte comprises a step of decreasing Brg1 activity. In an illustrative embodiment, Brg1 activity is decreased by introducing an interfering RNA (iRNA) to the cardiomyocyte to inhibit the translation of Brg1.

One aspect of the present disclosure is directed to nucleic acids comprising a myocardial eRNA. In one embodiment an isolated RNA comprising a sequence having at least 95% or 99% sequence identity with SEQ ID NO: 1 or 2, or a DNA equivalent is provided. In one embodiment an isolated DNA comprising a sequence having at least 95% or 99% sequence identity with SEQ ID NO: 5 or 6 is provided. In one embodiment the isolated RNA comprises the sequence of SEQ ID NO: 1 or 2, and in a further embodiment the isolated RNA consists of SEQ ID NO: 1 or 2. In one embodiment an isolated DNA is provided comprising the sequence of SEQ ID NO: 5 or 6, and in a further embodiment the isolated DNA consists of SEQ ID NO: 5 or 6.

In accordance with one embodiment, a nucleic acid is provided comprising the sequence of SEQ ID NO: 1 or its cDNA equivalent coupled to a marker. In some embodiments, the nucleic acid comprises a sequence consisting of SEQ ID NO: 1 or its cDNA equivalent coupled to a marker. In some embodiments, the marker is a detectable marker. In some embodiments, detectable the marker is selected from the group consisting of a fluorescent tag, an antibody, and a small peptide. In some embodiments, the detectable marker is coupled to an isolated nucleic acid comprising SEQ ID NO: 1 or its cDNA equivalent by a covalent linkage.

In some embodiments, a nucleic acid comprising a sequence comprising SEQ ID NO: 2 is disclosed. In some embodiments, the nucleic acid comprises a sequence comprising SEQ ID NO: 2 or its cDNA equivalent coupled to a marker. In some embodiments, the nucleic acid comprises a sequence consisting of SEQ ID NO: 2 or its cDNA equivalent coupled to a marker. In some embodiments, the marker is a detectable marker. In some embodiments, the detectable marker is selected from the group consisting of a radionuclide, fluorescent tag, an enzyme, an antibody, and small peptide. In some embodiments, the detectable marker is coupled to an isolated nucleic acid comprising SEQ ID NO: 2 or its cDNA equivalent by a covalent linkage.

In some embodiments a method of measuring Uhrt in a patient biological sample is provided. The method comprising, providing an RNA sample recovered from said patient, contacting the RNA sample with a nucleic acid that specifically binds to Uhrt, and detecting hybrids formed between the diagnostic nucleic acid and Uhrt as an indication of the presence and quantity of Uhrt in the patient sample. In one embodiment the diagnostic nucleic acid is a nucleic acid that is labeled with a detectable maker. In one embodiment the labeled diagnostic nucleic acid is an RNA sequence having at least 95% or 99% sequence identity with SEQ ID NO: 1 or 2. In one embodiment the labeled diagnostic nucleic acid is an RNA sequence comprising the sequence of SEQ ID NO: 1 or 2, and in a further embodiment the labeled diagnostic nucleic acid is an RNA sequence consisting of SEQ ID NO: 1 or 2. In one embodiment the labeled diagnostic nucleic acid is a DNA sequence comprising a sequence having at least 95% or 99% sequence identity with SEQ ID NO: 5 or 6, or its complement thereof. In one embodiment the labeled diagnostic nucleic acid comprises the sequence of SEQ ID NO: 5 or 6, and in a further embodiment the labeled diagnostic nucleic acid consists of SEQ ID NO: 5 or 6.

In some embodiments, the biological sample is heart tissue, blood, plasma, or a combination thereof, wherein the sample comprises cardiomyocytes RNA. In one embodiment the biological sample is a tissue or blood sample that comprises cardiomyocytes. In some embodiments, the biological sample is biopsy tissue sample comprising cardiomyocytes. In some embodiments, the sample is recovered during an operation, biopsy, or autopsy.

In one embodiment, the method of detecting and/or measuring the relative concentration of eRNA in a patient's cardiomyocytes comprises providing an RNA sample recovered from the patient and conducting quantitative reverse transcriptase polymerase chain reaction (rtPCR) to determined eRNA concentrations. In one embodiment the RNA sample is prepared from a tissue sample isolated from the patient, more particularly from a tissue or blood sample that comprises cardiomyocytes, using techniques known to those skilled in the art. The rtPCR is conducted using standard techniques known to the skilled practitioner, including a first step of converting the RNA present in the RNA sample to cDNA using reverse polymerase and a suitable set of primers. In one embodiment the reverse transcriptase reaction is conducted using a primer that specifically binds to the target eRNA (e.g., an eRNA comprising SEQ ID NO: 1 or 2 or derivative thereof). The generated cDNA is then amplified using standard PCR techniques and primers that specifically bind to Uhrt cDNA. Detection of the resulting amplicon as a measure of the Uhrt in the patient sample. In some embodiments, the resulting amplicon provides a measure of the relevant concentration of the Uhrt in the patient sample. In some embodiments, the PCR primers each comprise a sequence of at least 10 nucleotides, wherein the continuous primer sequence has at least 95% sequence identity to a corresponding equivalent fragment of SEQ ID NO: 2 or its compliment.

In some embodiments, a nucleic acid sequence is provided comprising a sequence of at least 10 nucleotides that has at least 95% sequence identity to a corresponding complementary portion of SEQ ID NO: 2 or its corresponding DNA equivalent or compliment thereof. In some embodiments, the nucleic acid is labeled with a detectable marker. In some embodiments, the detectable marker is selected from the group consisting of a fluorophore and radioisotope, and fluorophore. In some embodiments, the term "label" includes a covalent linkage or other known methods in the art of labeling nucleic acids.

In some embodiments, a method of identifying a patient at risk for hypertrophy is provided. The method comprises, providing a sample of RNA recovered from cardiomyocytes from the patient, analyzing the levels of Uhrt, and comparing the relative concentration levels of Uhrt in the patient cardiomyocytes to a reference sample.

In some embodiments, the reference sample comprises a known concentration of Uhrt. In some embodiments, the reference sample is a known concentration of Uhrt representing an amount of Uhrt expected in a patient sample not at risk for hypertrophy. The reference sample may vary depending on age, gender, and species of the patient. In some embodiments, the reference sample comprises an expected concentration of Uhrt in a normal fetal heart from a relevant population. In some embodiments, the reference sample comprises an expected concentration of Uhrt in a normal infant heart from a relevant population. In some embodiments, the reference sample comprises an expected concentration of Uhrt in a normal adolescent heart from a relevant population. In some embodiments, the reference sample comprises an expected concentration of Uhrt in a normal adult heart from a relevant population. In an illustrative embodiment, a low level of Uhrt RNA in the sample RNA recovered from cardiomyocytes compared to the reference sample identifies a patient at risk for hypertrophy.

In some embodiments, the analyzing step is performed using PCR, quantitative real-time PCR, Northern Blot, flow cytometry, mass spectrometry, molecular probes, or a combination thereof.

In some embodiments, a method of treating a patient at risk for heart disease is provided. In some embodiments, the heart disease is hypertrophy. The method comprises administering an isolated RNA sequence to the patient. In some embodiments, the RNA sequence comprises a sequence having at least 95% sequence identity to SEQ ID NO: 2 or its corresponding DNA equivalent. In some embodiments, the RNA sequence comprises a sequence having at least 90%, 91%, 92%, 93%, 94%, 95%, 96%, 97%, 98%, or 99% sequence identity to SEQ ID NO: 2 or its DNA equivalent.

In some embodiments, the method further comprises decreasing Brg1 activity. In an illustrative embodiment, Brg1 activity can be decreased by administering an iRNA to a cardiomyocyte designed to inhibit the translation of Brg1.

In some embodiments, the method further comprises analyzing Uhrt levels after the step of administering the RNA. In an illustrative embodiment, the step of analyzing may include performing PCR, rt-qPCR, Northern Blot, flow cytometry, mass spectrometry, the use of molecular probes, or a combination thereof.

In some embodiments, a method of switching a cardiomyocyte from a stressed-state to a non-stressed state is provided. The method comprising decreasing Brg1 activity and increasing Uhrt activity. In some embodiments, the Brg1 activity is decreased by providing a Brg1 iRNA. In some embodiments, the Uhrt activity is increased by providing a Uhrt RNA.

In one embodiment a method of detecting a patient at risk for hypertrophy is provided. The method comprises providing a test sample comprising RNA from the patient, contacting the test sample with a reverse transcriptase primer specific for an enhancer RNA comprising the sequence for Uhrt, reverse transcribing the enhancer RNA to produce a corresponding test cDNA, contacting the test cDNA with PCR primers specific for Uhrt RNA. In some embodiments, the primers comprise a sequence of at least 10 nucleotides having at least a 90% sequence identity to a corresponding complementary portion of SEQ ID NO: 2. In some embodiments, the primers comprise a sequence of at least 10 nucleotides having at least 91%, 92%, 93%, 94%, 95%, 96%, 97%, 98%, or 99% sequence identity to a corresponding complementary portion of SEQ ID NO: 2.

In some embodiments, the method further comprises conducting a PCR reaction on the test cDNA, and detecting the resulting amplified product. In some embodiments, the method further comprises determining the concentration of the enhancer RNA in the test sample based on the detected test cDNA. In some embodiments, the method further comprises obtaining a reference concentration of the corresponding enhancer RNA from a reference sample. In an illustrative embodiment, a detected low level of the enhancer RNA in the test sample as compared to the reference concentration level of the enhancer RNA indicates hypertrophy.

In some embodiments, a method of detecting a patient at risk for hypertrophy is provided. The method comprising providing a test sample comprising RNA from the patient; contacting the test sample with a reverse transcriptase primer specific for an enhancer RNA comprising the sequence for Uhrt; reverse transcribing the enhancer RNA to produce a corresponding test cDNA; contacting the test cDNA with PCR primers specific for Uhrt RNA wherein said primers comprise a sequence of at least 10 nucleotides having at least a 90% sequence identity to a corresponding complementary portion of SEQ ID NO: 2; conducting a PCR reaction on the test cDNA, and detecting the resulting amplified product; determining the concentration of the enhancer RNA in the test sample based on the detected test cDNA; and obtaining a reference concentration of the corresponding enhancer RNA; wherein a detected lower level of the enhancer RNA in the test sample as compared to the reference concentration level of the enhancer RNA indicates hypertrophy.

In accordance with embodiment 1 a method of inhibiting assembly of an enhancer DNA-Myh6 promoter-Myh7 promoter complex in a cardiomyocyte cell is provided. The method comprises the step of enhancing binding of Uhrt to said enhancer, wherein said enhancer comprises a sequence having at least 90, 95% or 99% sequence identity with SEQ ID NO: 3.

In accordance with embodiment 2, the method of embodiment 1 is provided wherein the Uhrt comprises an RNA sequence having at least 90, 95% or 99% sequence identity to SEQ ID NO: 2.

In accordance with embodiment 3, the method of embodiment 1 is provided wherein the Uhrt RNA comprises SEQ ID NO: 2 and said enhancer comprises SEQ ID NO: 3.

In accordance with embodiment 4, the method of embodiment 1 is provided wherein the Uhrt comprises an RNA sequence having at least 95% sequence identity to SEQ ID NO: 1.

In accordance with embodiment 5, the method of embodiment 1 is provided wherein the Uhrt RNA comprises SEQ ID NO: 1 and said enhancer comprises SEQ ID NO: 3.

In accordance with embodiment 6, the method of any one of embodiments 1-5 is provided wherein the method further comprising a step of decreasing Brg1 activity.

In accordance with embodiment 7, the method of embodiment 6 is provided wherein the Brg1 activity is decreased by introducing an interfering RNA into said cardiomyocyte cell to inhibit translation of Brg1.

In accordance with embodiment 8, a nucleic acid comprising an RNA sequence consisting of SEQ ID NO: 1, or its DNA equivalent thereof, coupled to a marker is provided.

In accordance with embodiment 9, a nucleic acid comprising an RNA sequence consisting of SEQ ID NO: 2, or its DNA equivalent thereof, coupled to a marker is provided.

In accordance with embodiment 10, the nucleic acid of embodiment 8 or 9 is provided wherein the marker is selected from the group consisting of a fluorescent tag, an antibody, and a small peptide.

In accordance with embodiment 11, a method of measuring Uhrt in a patient biological sample is provided. The method comprises:
  providing an RNA sample obtained from said patient;
  contacting the RNA sample with a nucleic acid that specifically binds to Uhrt; and
  detecting the Uhrt in the patient sample.

In accordance with embodiment 12, the method of embodiment 11 is provided wherein Uhrt is detected by quantitative reverse transcription PCR wherein an amplicon is only produced in the presence of Uhrt.

In accordance with embodiment 13, the method of embodiment 11 or 12 is provided wherein said RNA sample is reverse transcribed into cDNA and said cDNA is contacted with a pair of PCR primers wherein said primers each comprise a sequence of at least 10 nucleotides that each have at least 95% sequence identity to a corresponding DNA equivalent of SEQ ID NO: 2 or a compliment thereof.

In accordance with embodiment 14, the method of any one of embodiments 11-13 is provided wherein said nucleic acid comprises a sequence of at least 10 nucleotides that has at least 95% sequence identity to a corresponding complementary portion of SEQ ID NO: 2 or its corresponding DNA equivalent or compliment thereof, wherein said nucleic acid is labeled with a detectable marker.

In accordance with embodiment 15, the method of embodiment 14 is provided wherein the detectable marker is selected from the group consisting of a fluorophore and a radioisotope and a fluorophore.

In accordance with embodiment 16, a method of identifying a patient at risk for hypertrophy is provided. The method comprises:
  providing a sample of RNA recovered from cardiomyocytes from the patient;
  analyzing the levels of Uhrt RNA in said sample; and
  comparing the Uhrt RNA levels in the patient cardiomyocytes to a reference sample, wherein a low level of Uhrt RNA compared to the reference sample identifies a patient at risk for hypertrophy.

In accordance with embodiment 17, the method of embodiment 16 is provided wherein the reference sample is either a set of values based on population data (i.e., average concentration of a molecule in a target population) or the detected eRNA levels in a sample recovered from an individual or from a control population know to lack the relevant genotypic or phenotypic characteristic (e.g., low levels of eRNA, optionally the RNA of SEQ ID NO: 1 or 2) associated with hypertrophy.

In accordance with embodiment 18, a method of identifying a patient at risk for heart disease is provided. The method comprises:
  administering an RNA sequence to the patient, wherein the RNA sequence comprises a sequence having at least 95% sequence identity to SEQ ID NO: 2 or its corresponding DNA equivalent thereof.

In accordance with embodiment 19, the method of embodiment 18 is provided wherein the heart disease is hypertrophy.

In accordance with embodiment 20, the method of embodiment 18 or 19 is provided wherein the method further comprises decreasing Brg1 activity.

In accordance with embodiment 21, a method of switching a cardiomyocyte from a stressed-state to a non-stressed state is provided wherein the method comprises:
  decreasing Brg1 activity, and
  increasing Uhrt activity, wherein the cardiomyocyte is switched from a stressed-state to a non-stressed state.

In accordance with embodiment 22, the method of embodiment 21 is provided wherein decreasing the Brg1 activity comprises providing a Brg1 interfering RNA.

In accordance with embodiment 23, the method of embodiment 21 or 22 is provided wherein the step of increasing of Uhrt activity comprises providing a Uhrt RNA.

EXAMPLE 1

We identified a cardiac-specific enhancer, situated upstream of its target myosin heavy chain genes (Myh6 and Myh7), that gave rise to a cardioprotective eRNA, which we named Uheart (Uhrt) for Upstream Myosin Heavy chain RNA Transcript. In fetal mouse hearts, the enhancer produced little Uhrt and actively looped to Myh6 and Myh7 promoters, forming an enhancer-Myh6-Myh7 triplex to trigger antithetical Myh regulation—Myh7 up- and Myh6 down-regulation—to maintain Myh in fetal status. As the heart matured, the enhancer robustly transcribed Uhrt, which inhibited enhancer's looping to its target Myh promoters, switching fetal Myh to adult status. Upon cardiac stress, Uhrt transcription was shut down, and the enhancer regained its looping to Myh loci, triggering Myh switch and hypertrophy. Mechanistically, enhancer-Myh looping required the chromatin remodeler Brg1 to recruit the looping regulator CTCF to the enhancer. Binding of CTCF to the enhancer was inhibited by Uhrt, which tethered to the enhancer to form RNA-DNA hybrid, preventing CTCF binding. Cardiac stress stimulated Brg1 to bind to Uhrt-DNA hybrid and recruit Senataxin—an RNA-DNA helicase—to unwind the hybrid and restore DNA duplex, enabling CTCF to bind and trigger enhancer looping and Myh switch. Termination of Uhrt transcription unleashed the enhancer and sensitized the hearts to stress-induced hypertrophy. The enhancer-UHRT interaction was conserved in human hearts. Our studies thus identify a new cardioprotective eRNA, exemplifying a novel eRNA function in enhancer silencing and disease biology.

Inactive/poised enhancers were excluded from eRNA investigations due to the lack of specific chromatin markers to align with eRNA transcription profiles. The current model indicates that eRNAs are either transcriptional noises that mark activated enhancers or are capable of facilitating enhancer function by enabling enhancer looping to target promoters or by scaffolding enhancer-promoter structure. To the best of our knowledge, there has been no description of eRNAs transcribed from inactive enhancers and capable of keeping the enhancers silent. We found an unconventional eRNA that prevents enhancer-promoter interactions to regulate molecular motor gene expression and cardiac pathophysiology. The molecular motor myosin heavy chain Myh6 and Myh7 control the contraction of mammalian hearts. The relative amount of Myh6 and Myh7 changes under different pathophysiological conditions, correlating with heart function in animals and in patients with cardiomyopathy. Myh genes are regulated antithetically—with up-regulation of one isoform always accompanied by down-regulation of the other—and their ratio governs cardiac resistance to pathological hypertrophy. Hearts expressing more Myh6 show resistance to pathological stress; those expressing more Myh7 are susceptible. The new eRNA-enhancer interaction provides a mechanism that coordinates antithetical Myh changes to control cardiac contractility and resistance to stress. It also provides a therapeutic strategy to shut down Myh7, the mutations of which are the underlying causes of disease in many patients with hypertrophic or dilated cardiomyopathy.

In Vitro Transcription of Single Guide RNA (sgRNA) for Mouse Injection

The 20-bp spacer sequence specific to target locus was designed by deskgen (www.deskgen.com). DNA template for sgRNA in vitro transcription was PCR-amplified from pX330 plasmid (42230, Addgene) to acquire a fused DNA template containing the T7 promoter at 5' end, spacer sequence, and transactivating CRISPR RNA (tracrRNA) sequence at 3' end. The PCR product was gel purified (28704, Qiagen) for in vitro transcription using MEGAshortscript T7 Kit (AM1354, Thermo Fisher Scientific), and the RNA was purified with miRNeasy Mini Kit (217004, Qiagen) for mouse injection. 20-bp spacer sequences of sgRNAs for eDNA$^{f/f}$ mouse line are CAACCCTGAGCACGTGGAGC (SEQ ID NO: 7) and GGCTTAAGAGATCCTCTTGG (SEQ ID NO: 8). Spacer sequence of sgRNA for both Uhrt knockout mouse line and Uhrt CMV knockin (Uhrt KI) is ACACTATGAGATGGACTCGC (SEQ ID NO: 9).

Developmental Day Determination and Mouse Line Generation

The date of observing of a vaginal plug was set as embryonic day E0.5 by convention. Mouse lines Sm22α-Cre, Brg1$^{f/f}$, and Tnnt2-rtTA;Tre-cre were previously described. CD1 mice were purchased from Charles River (Strain Code: 022). The eDNA$^{f/f}$ mouse line was generated using the CRISPR/Cas9 system by cytoplasmic injection of mouse embryos with sgRNAs, Cas9 mRNA (L-6129, TriLink Biotechnologies) and single-stranded DNA donors containing loxP sequence (IDT, Ultramer DNA Oligonucleotides). B6D2F1 (C57BL/6×DBA2, Charles River) female mice and CD1 mouse strains were used as embryo donors and foster mothers, respectively. Superovulated female B6D2F1 mice (4-week-old) were mated to B6D2F1 stud males to collect fertilized embryos. Zygotes were harvested and kept in M16 medium (M7292, Sigma) at 37° C. for 1 hr and then transferred in M2 medium (M7167, Sigma) to inject sgRNAs, Cas9 mRNA and single-stranded DNA donors. Injected zygotes were cultured in M16 medium for 1 hr at 37° C. before transferred into the oviducts of pseudopregnant CD1 female mice. For Uhrt knockout mouse line, the Uhrt-tdTO3×polyA donor vector was generated by cloning homology arms of 2.5-3-kb on either side that is specific to the targeted endogenous locus at the 89-bp from mouse Uhrt transcriptional start site into tdTO3×polyA vector. The donor vector was then mixed with sgRNA and Cas9 mRNA for cytoplasmic injection.

Transgenic mice were derived by pronuclear injection of mouse embryos. For enhancer DNA reporter lines (eDNA-lacZ or heDNA-lacZ), mouse or human enhancer DNA was subcloned into pENTR/TEV/D-TOPO donor vector (K253520, Thermo Fisher Scientific), and gateway recombination was performed with hsp68-lacZ destination vector (37843, Addgene) to generate eDNA-hsp68-lacZ reporter for mouse injection. For Uhrt reporter lines (CMV-eDNA-lacZ and CMV-heDNA-lacZ), mouse Uhrt or human UHRT cDNA was subcloned into a modified pcDNA3.1(+) vector whose CMV promoter was surrounded by two loxP sites. A fragment containing both loxP, CMV, Uhrt/UHRT cDNA and SV40 polyA terminator (pA) was subcloned into pENTR/TEV/D-TOPO donor vector and recombined into the hsp68-lacZ destination vector by gateway reaction to generate LoxP-CMV-loxP-Uhrt-pA-hsp68-lacZ or LoxP-CMV-loxP-UHRT-pA-hsp68-lacZ plasmid. These plasmids were then linearized for pronuclear injection.

LacZ Reporter Assay

Whole-mount X-gal staining was performed using X-gal staining kit (K146501, Thermo Fisher Scientific) following the manufacturer's instruction. E11.5 embryos were fixed in 4% paraformaldehyde/PBS on ice for 30 min. For adult heart tissues, 7-μm sections were acquired using a Leica cryostat and air-dried for 5 min. 4% paraformaldehyde/PBS was added on the section and fixed for 10 min at room temperature, followed by washing with PBS for 3 times. Embryos or sections were then processed for X-gal staining.

Chromosome Conformation Capture with Quantitative PCR (3C-qPCR)

3C-qPCR was performed following the protocol described with modifications. Briefly, embryonic mouse hearts were collected and cross-linked with 1% formaldehyde immediately. Adult hearts were cut into pieces on ice and homogenized in 1% formaldehyde immediately and incubated at room temperature for 15 min with rotation, followed by standard glycine quenching. After centrifuge (2,000 g×5 min), pellets were resuspended in ice-cold PBS and pass the tissue strainer (250 μm) for centrifuge. The pellets were resuspended in cytoplasmic lysis buffer (10 mM HEPES, 60 mM KCl, 1 mM EDTA, 0.1% (v/v) NP40, 1 mM DTT and 1 mM PMSF, pH 7.6) and incubated on ice for 30 min and then centrifuged (2,000 g×5 min) to collect cross-linked nuclei. Nuclei was washed with restriction enzyme buffer and resuspended in restriction enzyme buffer with 0.3% SDS and incubated with shaking at 1400 rpm overnight at 37° C. 2× volume of restriction enzyme buffer was added to disperse the aggregations. SDS was sequestered by adding Triton X-100 (1.8% of final concentration) and incubated with shaking at 1400 rpm for 2 hr at 37° C. Restriction enzyme was then added and incubated with shaking at 1400 rpm overnight at 37° C. In the next day, SDS was added into the buffer (1.6% of final concentration) and incubated with shaking at 1400 rpm for 30 min at 65° C. to stop the digestion. A 7-ml ligation reaction system was established with T4 DNA ligase (M0202, New England Biolabs) and DNA at the final concentration less than 1 ng/μl to favor intramolecular ligation. Ligation was performed overnight at 16° C. with rotation. Reverse-cross-link was performed by adding 5 M NaCl, 1 M EDTA and Proteinase K into the ligation mix overnight at 65° C. followed by phenol/chloroform extraction and ethanol precipitation. The 3C library was amplified in 5-7 PCR cycles using Phusion polymerase (M0530, New England biolabs) and diluted for nested quantitative PCR. For Myh6-eDNA and Myh6-Myh7 interactions, CSP6I (ER0211, Thermo Fisher Scientific) was used for digestion. The genomic area +1192 to −1892 from Myh6 transcriptional start site generated by CSP6I digestion was used for determining Myh6-eDNA interaction. The genomic area +1237 to +2911 from Uhrt transcriptional start site generated by CSP6I digestion was used for determining Myh6-eDNA interaction. The genomic area −147 to −1302 from Myh7 transcriptional start site generated by CSP6I digestion was used for determining Myh6-Myh7 interaction. For Myh7-eDNA, MSPI (R0106, New England Biolabs) was used for digestion. The genomic area +2263 to −1093 from Myh7 transcriptional start site generated by MSPI digestion was used for determining Myh7-eDNA interaction. The genomic area +528 to +1665 from Uhrt transcriptional start site generated by MSPI digestion was used for determining Myh7-eDNA interaction.

Chromosome Conformation Capture Carbon Copy (5C)

For 5C library preparation, 3C library was denatured at 95° C. for 5 min with salmon testis DNA (Sigma) and 5C oligonucleotides in annealing buffer (20 mM Tris-acetate at pH 7.9, 50 mM potassium acetate, 10 mM magnesium acetate, and 1 mM DTT), followed by annealing for 16 h at 48° C. Annealed primers were ligated for 1 h at 48° C. by adding 20 μL of ligation buffer (25 mM Tris-HCl at pH 7.6, 31.25 mM potassium acetate, 12.5 mM magnesium acetate, 1.25 mM NAD, 12.5 mM DTT, 0.125% Triton X-100) containing 10 units of Taq DNA ligase (NEB). Unincorporated primers were removed by MinElute Reaction Cleanup Kit (Qiagen). 5C ligation products were amplified by PCR using specific 5C primers for each looping reaction as follow.

```
Myh7-eDNA 5C-F,
                               (SEQ ID NO: 10)
TAATACGACTCACTATAGCCTTGTCTTCCC

Myh7-eDNA 5C-R,
                               (SEQ ID NO: 11)
TATTAACCCTCACTAAAGGGAAGCCCAGA

Myh6-eDNA 5C-F,
                               (SEQ ID NO: 12)
TAATACGACTCACTATAGCCGCTCTTGAG

Myh6-eDNA 5C-R,
                               (SEQ ID NO: 13)
TATTAACCCTCACTAAAGGGACCTAAACCTC

Myh6-Myh7 5C-F,
                               (SEQ ID NO: 14)
TAATACGACTCACTATAGCCCTTGAGGG

Myh6-Myh7 5C-R,
                               (SEQ ID NO: 15)
TATTAACCCTCACTAAAGGGAATGGGCTG.
```

Chromatin Immunoprecipitation Quantitative PCR (ChIP-qPCR)

Embryonic mouse hearts were collected and cross-linked immediately. For adult hearts, tissues were cut into pieces on ice, homogenized with 1% formaldehyde immediately and incubated at room temperature for 15 min with rotation. Glycine was then added to quench the cross-link reaction and pass the tissue strainer (250 μm) (87791, Thermo Fisher Scientific). After centrifuge (2,000 g×5 min), the pellets were resuspended in nuclei lysis buffer (1% SDS, 10 mM EDTA, 50 mM Tris, pH 8.1) for sonication to shear chromatin with Bioruptor (Diagenode) (30 s on, 30 s off, power setting H, 30 min, twice) to generate the fragments at the range of 100-300 bp. Sonicated chromatin was pre-cleaned by ChIP-Grade Protein G magnetic beads (9006, Cell Signaling Technologies) and immunoprecipitated with anti-Brg1 J1 antibody, anti-CTCF (61311, Active motif), anti-RPA (MABE285, Millipore) or anti-Senataxin (ABN421, Millipore) overnight. ChIP-Grade Protein G magnetic beads were added to collect the immunoprecitate complex and washed once with low salt wash buffer (0.1% SDS, 1% Triton X-100, 2 mM EDTA, 20 mM Tris-HCl, pH 8.1, 150 mM NaCl), high salt wash buffer (0.1% SDS, 1% Triton X-100, 2 mM EDTA, 20 mM Tris-HCl, pH 8.1, 500 mM NaCl), LiCl wash buffer (0.25 MLiCl, 1% IGEPAL-CA630, 1% deoxycholic acid (sodium salt), 1 mM EDTA, 10 mM Tris, pH 8.1) and twice with TE buffer (10 mM Tris-HCl, 1 mM EDTA, pH 8.0). Quantitative PCR was then performed with primers as follows. Mouse ChIP-eDNA-F, CTTCGTATCAGGGGGTGTTCC (SEQ ID NO: 16) Mouse ChIP-eDNA-R, GAAGGGGTTGGAAGGTCACT (SEQ ID NO: 17).

Transaortic Constriction (TAC)

The TAC surgery was performed on adult mice of 8-10 weeks of age and between 20 and 25 g of weight. Mice were fed with doxycycline food pellets (6 g doxycycline per kg of food; Bioserv) 7 days before the TAC operation if needed. Mice were anaesthetized with isoflurane (3%, inhalation) in an induction chamber and endotracheal intubation was performed with a 20-gauge intravenous catheter and ventilated with a mouse ventilator (Minivent, Harvard Apparatus) to maintain anesthesia with haled isoflurane (1-2%). A longitudinal 5 mm incision of the skin was made with scissors at the midline of sternum. The chest cavity was opened by a small incision at the level of the second intercostal space 2-3 mm from the left sternal border and two chest retractors were gently inserted to spread the wound 4-5 mm in width to expose the transverse portion of the aorta. A nonabsorbable 6-0 suture is brought by one ligation aid and moved underneath the transverse aorta between the left common carotid artery and the brachiocephalic trunk to make a loose knot. For aortic constriction, 27-gauge needle was placed directly above and parallel to the aorta. The knot was then tied around the aorta and needle, and secured with a second knot. The needle was removed from the knot carefully to create a lumen with a fixed stenotic diameter. The chest cavity was then closed by 6-0 silk suture Sham operated mice underwent similar surgical procedures, including isolation of the aorta and looping of the aorta, but without tying of the suture. The TAC was verified and qualified by the pressure gradient across the aortic constriction measured by echocardiography. Only mice with a pressure gradient 30 mmHg were used for further experiments and analysis.

Echocardiography

Transthoracic ultrasonography was performed with a GE Vivid 7 ultrasound platform (GE Health Care) equipped with a 13 MHz transducer to determine aortic pressure gradient and left ventricular function at the time points as indicated. The echocardiographer was blinded to the genotypes and surgical procedure. The isoflurane (inhalational) was adjusted to anaesthetize the mice while maintaining their heart rates at 450-550 beats per minute to minimize its effects on heart rates. The peak aortic pressure gradient was measured by continuous wave Doppler across the aortic constriction. Left ventricular function was assessed by M-mode scanning of the left ventricular chamber, standardized by two-dimensional, short-axis views of the left ventricle at the mid papillary muscle level. Left ventricular chamber size and wall thickness were measured in at least three beats from each projection and averaged. Left ventricular internal dimensions at diastole and systole (LVIDd and LVIDs, respectively) were measured. The fractional shortening (FS) of the left ventricle was defined as (1 minus LVIDs/LVIDd)×100%. The mean FS of the left ventricle was determined by the average of FS measurements of the left ventricular contraction over five beats. P values were calculated by Student's t-test. Error bars indicate standard error of the mean (SEM).

Rapid Amplification of cDNA Ends (RACE) and Uhrt Cloning

The 5' and 3' RACE were performed using the SMARTer® RACE 5'/3' kit (634858, Takara Bio) following the manufacturer's instruction. Total RNA of adult mouse hearts was extracted by TRIzol and used as template. Primers used for 5' RACE (GCCTAGGGGCCTGTGGCCTCTTGG; SEQ ID NO: 18) and 3' RACE (CCAAGAGGCCACAGGCCCCTAGGC; SEQ ID NO: 19). Once the 5' and 3' cDNA ends were reached, common primers were used to amplify full-length Uhrt transcripts, which were subcloned into pCR II TA cloning vector for sequencing. For human UHRT, total RNA of adult human hearts was purchased from Takara Bio (636532) as template. Primers used for 5' RACE (TACCTCTCTATCCTCTTGTCCAATGACATTGCC; SEQ ID NO: 20) and 3' RACE (GGAGGGGGGTGG-CATGACTCTTGGAAGA; SEQ ID NO: 21). Once the 5' and 3' cDNA ends were reached, common primers were used to amplify full-length UHRT transcripts, which were subcloned into pCR II TA cloning vector for sequencing.

Northern Blot Analysis and In Vitro Translation

Northern blot analysis was performed using the DIG Northern Starter Kit (12039672910, Roche) with 5 ug total RNAs from adult mouse hearts. Single-stranded RNA probe template was generated by PCR with a forward primer containing the T7 promoter. Single-stranded RNA was then in vitro transcribed with labeling mix in the kit to label the RNA with digoxigenin. For in vitro translation, full-length RNAs were transcribed and performed in vitro translation using the PURExpress Kit (E6800, New England biolabs). To label synthesized protein, Transcend-tRNA (L506A, Promega) was added into the translation reaction system.

Codon Substitution Frequency (PhyloCSF) and Ribosome Profiling (Ribo-Seq)

To measure the coding potential of mouse Uhrt and human UHRT, we used PhyloCSF software to compute the score for how likely each sequence represents a conserved coding region. We used multi-species alignment between human, mouse, rat, rhesus and dog for each gene as input for PhyloSCF. The options used for PhyloSCF are ATGStop for sequences with full ORF, and Asis for other sequences.

Ribosomal profiling was performed using mammalian TruSeq Ribo Profile (RPHMR12126, Illumina) following the manufacture's instruction with modifications described below. Mouse adult hearts were dissected and rinsed in ice-cold PBS with 8 mg/ml cycloheximide (2112, Cell Signaling Technologies) for 5 min. Tissues were then cut into pieces and homogenized with lysis buffer in the kit. Lysates were treated with ARTseq nuclease and the ribosome protected fragments were isolated using MicroSpin S-400 columns (27514001, GE Healthcare). rRNAs were depleted by Ribo-Zero Gold rRNA Removal kit (MRZG126, Illumina) and ribosome-protected fragments were amplified in 9 PCR cycles using Phusion polymerase and purified by 10% Novex™ TBE-Urea Gels (EC6875BOX, Thermo Fisher Scientific). Libraries were sequenced on HiSeqSE50 platform. Reads were mapped to mm10 build of the mouse genome using TopHat2.

Quantitative Reverse Transcription PCR (RT-qPCR)

Total RNA was extracted by TRIzol, and reverse transcription was performed with PrimeScript™ RT reagent Kit (RR036a, Takara Bio). For strand-specific reverse transcription, SuperScript™ VILO™ cDNA Synthesis Kit (Ser. No. 11/754,050, Thermo Fisher Scientific) was used with specific primers (Mouse: GAGGCATCCGATCCCATTA-CAGA (SEQ ID NO: 22); human: CTTCCCAC-TACCTCTCTATC (SEQ ID NO: 23). RT-qPCR was then performed using Power SYBR Green PCR Master Mix (4367659, Thermo Fisher Scientific) with StepOnePlus Real-time PCR System (Thermo Fisher Scientific). Transcription factor IIb (TfIIb) was used as a normalizer. Threshold cycles and melting curve measurements were performed with ABI software. Primers for RT-qPCR of mRNA were as follows.

```
Mouse TfIIb-F,
                                   (SEQ ID NO: 24)
CTCTGTGGCGGCAGCAGCTATTT);

Mouse TfIIb-R,
                                   (SEQ ID NO: 25)
CGAGGGTAGATCAGTCTGTAGGA;

Mouse Myh6-F,
                                   (SEQ ID NO: 26)
ACGGTGACCATAAAGGAGGA;

Mouse Myh6-R,
                                   (SEQ ID NO: 27)
TGTCCTCGATCTTGTCGAAC;

Mouse Myh7-F,
                                   (SEQ ID NO: 28)
GCCCTTTGACCTCAAGAAAG;

Mouse Myh7-R,
                                   (SEQ ID NO: 29)
CTTCACAGTCACCGTCTTGC;

Mouse Uhrt-F,
                                   (SEQ ID NO: 30)
TCAGTCTGTGGCCTAAGCTC;

Mouse Uhrt-R,
                                   (SEQ ID NO: 31)
TGAACTCGGCAAGTCCCTC;

Human TfIIb-F,
                                   (SEQ ID NO: 32)
GAGCAGTTCTGATCGGGCAA;

Human TfIIb-R,
                                   (SEQ ID NO: 33)
CGAGGGTAGATCAGTCTGTAGGA;

Human Myh6-F,
                                   (SEQ ID NO: 34)
TTCAGGATTCTCCGTGAAGGG;

Human Myh6-R,
                                   (SEQ ID NO: 35)
GTCGAACTTGGGTGGGTTCT;

Human Myh7-F,
                                   (SEQ ID NO: 36)
GAGCTCACCTACCAGACGGA;

Human Myh7-R,
                                   (SEQ ID NO: 37)
CCTCATTCAAGCCCTTCGTG;

Human UHRT-F,
                                   (SEQ ID NO: 38)
AGTGGCCCCAAGGTGTTAAG;
and Human UHRT-R,
                                   (SEQ ID NO: 39)
CGCGTGCACCTATTCTCTCT.
```

Cytoplasmic, Nuclear and Chromatin-Associated RNA Fraction

To isolate cytosolic and nuclear RNAs from adult hearts, 10 μg hearts were homogenized in cell fractionation buffer from PARIS kit (AM1921, Thermo Fisher Scientific), followed by centrifuge (500 g×5 min). The supernatants (set as the cytosolic fraction) and the pellets were washed twice and lysed in cell disruption buffer on ice. TRIzol was then added into both fractions to extract RNA for RT-qPCR. To isolate chromatin-associated RNAs, nuclei pellets were first rinsed in glycerol buffer (20 mM Tris-HCl, pH 7.9, 75 mM NaCl, 0.5 mM EDTA, 0.85 mM DTT, 0.125 mM PMSF, 50% glycerol) and equal volume of cold nuclei lysis buffer (10 mM HEPES, pH 7.6, 1 mM DTT, 7.5 mM $MgCl_2$, 0.2 mM EDTA, 0.3 M NaCl, 1 M UREA, 1% NP-40) was added and incubated for 10 min on ice with vortex for 2 times for each 5-min interval. After centrifuge (12,000 g×10 min), the supernatants were collected as nucleoplasma, and the pellets as chromatin. Pellets were washed twice with cold nuclei lysis buffer. TRIzol was then added into both fractions to extract RNA for RT-qPCR.

Cardiomyocyte Isolation

Cardiomyocytes were isolated from the ventricles of adult mice using enzymatic digestion on a Langendorff system with constant retrograde perfusion and pressure measurement. Enzyme digestion solution was made with $Ca^{2+}$ (12.5 μM), collagenase type II (300 U/ml, LS004174, Worthington Biochemicals), and protease type XIV (0.04 mg/ml, P5147, Sigma) in Tyrode's solution (133.5 mM NaCl, 4.0 mM KCl, 1.2 mM $NaH_2PO_4$, 10 mM HEPES, 1.2 mM $MgSO_4$, and 10 mM glucose; pH=7.4, adjusted with NaOH) Ventricular myocytes were resuspended in Tyrode's solution containing 1 mg/ml BSA and centrifuged at 46 g×3 min, and the cardiomyocyte pellets were collected. The supernatants were further centrifuged at 46 g×3 min to discard the pellets, and the cell suspensions were centrifuged at 300 g×10 min $CD31^+$ endothelial cells were then isolated from the pellets using mouse CD31 MicroBeads (130097418, Miltenyi). Remaining cells were collected as cardiac fibroblasts.

Histology, Trichrome Staining, and Morphometric Analysis of Cardiomyocytes

Adult hearts were dissected and fixed overnight in 4% paraformaldehyde/PBS, followed by dehydration through an ethanol series, treated with xylenes, and embedded in paraffin wax overnight. 7 μm sections were then acquired using a Leica microtome. After re-hydration, the sections were stained with trichrome stain (Masson) kit (HT15-1KT, Sigma) following the manufacturer's instruction. Fluorescein isothiocyanate-conjugated wheat germ agglutinin (WGA) was used to visualize the cell border of cardiomyocytes in paraffin sections. Cardiomyocytes of the papillary muscle at the mid-left ventricular cavity were selected for cardiomyocyte size. The images were acquired by fluorescence microscope (Nikon Eclipse Ni) equipped with HAMAMATSU imaging system.

Strand-Specific DNA-RNA Immunoprecipitation with Quantitative Reverse Transcription PCR (DRIP-RT-qPCR)

Embryonic or adult hearts were collected and digested with lysis buffer (0.5% SDS, 2 mM EDTA, 10 mM Tris-HCl, pH 8.1, 100 mM NaCl). Genomic DNA was then extracted by phenol/chloroform and precipitated by ethanol. 5 μg genomic DNA was further digested by a combination of BsoB1, NheI, NcoI and StuI overnight at 37° C. with or without RNase H (M0297, New England Biolabs) and followed by phenol/chloroform extraction and ethanol precipitation. Digested DNA was then rinsed in 500 μl binding buffer (1% Triton X-100, 50 mM Tris-HCl, 75 mM KCl, 3 mM $MgCl_2$, 10 mM DTT) and pre-cleaned by ChIP-Grade Protein G magnetic beads. Anti-DNA-RNA hybrid S9.6 antibody (ENH001, Kerafast) was then incubated with the digested DNA overnight at 4° C. with rotation. The immunoprecipitated complex was washed once with low salt wash buffer (0.1% SDS, 1% Triton X-100, 2 mM EDTA, 20 mM Tris-HCl, pH 8.1, 150 mM NaCl), high salt wash buffer (0.1% SDS, 1% Triton X-100, 2 mM EDTA, 20 mM Tris-HCl, pH 8.1, 500 mM NaCl), LiCl wash buffer (0.25 M LiCl, 1% IGEPAL-CA630, 1% deoxycholic acid (sodium salt), 1 mM EDTA, 10 mM Tris, pH 8.1) and twice with TE buffer (10 mM Tris-HCl, 1 mM EDTA, pH 8.0) and then treated by proteinase K at 65° C. with agitation. DNA/RNA hybrid was extracted by phenol/chloroform, precipitated by ethanol, and digested with TURBO™ DNase (AM2238, Thermo Fisher Scientific). TRIzol was then added to extract RNA, and strand-specific reverse transcription was performed with SuperScript™ VILO™ cDNA Synthesis Kit.

Western Immunoblot Analysis

Whole hearts were collected and homogenized in buffer A (25 mM HEPES, pH 7.0, 25 mM KCl, 5 mM $MgCl_2$, 0.05 mM EDTA, 10% glycerol, 0.1% NP-40). After lysis of heart tissues on ice for 10 min, nuclear pellets were collected and resuspended in buffer B (50 mM Tris-Hcl, pH 6.8, 2% SDS, 100 mM DTT, 10% glycerol) and lysed on ice for 30 min. After centrifuge, the supernatants were collected and boiled. The blots were reacted with antibodies for CTCF (61311, Active motif), Senataxin (ABN421, Millipore), and TFIIB (ab109518, Abcam) followed by HRP-conjugated anti-rabbit IgG (211-032-171, Jackson ImmunoResearch Laboratories). Chemiluminescence was detected with Pierce™ ECL Plus Western Blotting Substrate (32134, Thermo Fisher Scientific) and visualized by Odyssey Image System (LI-COR).

Electrophoretic Mobility Shift Assay (EMSA)

EMSA was performed by using LightShift™ Chemiluminescent RNA EMSA Kit (20158, Thermo Fisher Scientific) following the manufacture's instruction. For RNA-DNA hybrid probe, a DNA oligo containing the T7 promoter (lowercase) and a CTCF binding sequence (uppercase) from the mouse eDNA locus with CTCF consensus binding motif (underlined) and surrounding sequences

```
(ttaatacgactcactataggTCAGCCACACAACAG

AGGGGGTGGCACAGCTCTTGGGA (SEQ ID NO: 40)),
``` as well as its reverse complementary DNA oligo, were synthesized (Thermo Fisher Scientific) and annealed for In vitro transcription with MEGAshortscript T7 Kit. Given the RNA product contains two more guanine nucleotides (lowercase) at 5' end by T7 RNA polymerase (ggTCAGC-CACACAACAGAGGGGGTGGCACAGCTCTTGGGA (SEQ ID NO: 41)), its 5' biotin-labeled reverse complementary DNA oligo was introduced 2 more cytosine nucleotides at 3' end to acquire a blunt-ended probe. For double-stranded DNA probe, a DNA oligo with the same sequence as RNA was synthesized and annealed with the biotin-labeled reverse complementary DNA oligo. A mutant probe was synthesized with a mutated CTCF consensus binding motif (ggTCAGC-CACACAACAGAAAAAATGGCACAGCTCTTGGGA (SEQ ID NO: 42)). All these biotin-labelled probes were incubated with 200 ng CTCF recombinant proteins (H00010664-P01, Abnova) in 20 µl 1× binding buffer (10 mM HEPES-KOH, pH 7.3, 10 mM NaCl, 1 mM $MgCl_2$, 1 mM DTT) with 5 µg tRNA carrier at room temperature for 30 min. The reactions were then loaded onto 6% Novex TBE gels (EC6265BOX, Thermo Fisher Scientific) and transferred to Bright Star-Plus positive charged membrane (AM10110, Thermo Fisher Scientific). Biotin-labeled probes were detected by Chemiluminescent Nucleic Acid Detection Module (89880, Thermo Fisher Scientific) using Odyssey Imaging System (LI-COR).

Amylose Pull-Down 20 pmol purified Maltose-binding protein (MBP) or MBP-Brg1 D1D2 protein was incubated with Amylose Magnetic Beads (E8035, New England Biolabs) for 2 hr at 4° C. with rotation. After washed three times with MBP column binding buffer (10 mM Tris-HCl, pH7.5, 150 mM NaCl, 1 mM DTT, 0.1% Triton X-100), the beads were resuspended in 500 µl binding buffer. 20 pmol of 200-bp single stranded DNA (ssDNA) probe containing the CTCF binding motif in the eDNA (chr14:55,004,492-55,004,691, mm10), single stranded RNA (ssRNA) probe with the same sequence as the ssDNA, and DNA-RNA hybrid probe annealed from the ssRNA and its complementary DNA were incubated with the beads for 2 hr at 4° C. with rotation and washed three times with low salt wash buffer (0.1% SDS, 1% Triton X-100, 2 mM EDTA, 20 mM Tris-HCl, pH 8.1, 150 mM NaCl) and three times with high salt wash buffer (0.1% SDS, 1% Triton X-100, 2 mM EDTA, 20 mM Tris-HCl, pH 8.1, 500 mM NaCl). The beads were then eluted with elution buffer (10 mM Tris-HCl, pH7.5, 150 mM NaCl, 1 mM DTT, 0.1% Triton X-100, 10 mM maltose). Proteinase K was incubated with the elution buffer at 65° C. for 1 hr and the probes were purified by miRNeasy Mini Kit (217004, Qiagen). Reverse transcription was performed for ssRNA samples with SuperScript™ VILO™ Master Mix (Ser. No. 11/755,050, Thermo Fisher Scientific). All samples were then performed with qPCR analysis.

Motif Prediction

MEME Suite was used for motif discovery as described. Briefly, all sequences from different species were trimmed to the same size and subjected to MEME-ChIP using JASPAR-_CORE_2009. MEME motif database. CentriMo from MEME Suite was used to calculate different motifs distribution. FindMotif tools from HOMER were used to confirm the results from MEME Suite.

RNA Secondary Structural Prediction and DNA Homology Score

To predict the secondary structure for mouse Uhrt and human UHRT, their sequences were submitted on Vienna RNA fold web server (http://rna.tbi.univie.ac.at/cgi-bin/RNAfold.cgi) with calculation of minimum free energy. To score the sequence homology of mouse and human eDNA, as well as mouse Uhrt and human UHRT, respective sequences were submitted on T-coffee for analysis (https://www.ebi.ac.uk/Tools/msa/tcoffee/).

Human Heart Tissue Analysis

Human heart samples were obtained from Duke Human Heart Repository (https://sites.duke.edu/dhhr/) and as described. The study of human tissues is in compliance with the regulation of Duke and Indiana University. Human tissues were processed for RT-qPCR. Other human tissue RNAs were purchased from Takara Bio.

Statistical Analysis

Statistical significances were calculated using GraphPad Prism 6 (GraphPad Software, La Jolla, CA) or SPSS 25 (IBM, Armonk, New York). Differences between two groups were compared by student's t-test, and differences among multiple groups were compared by one-way ANOVA analysis of variance. All significance levels were computed as 2-tailed and a value of $P<0.05$ was considered statistically significant.

EXAMPLE 2

By surveying cardiac chromatin modifications in ENCODE database, we identified a genomic region 7.5-kb upstream of the mouse Myh7 gene transcriptional start site that spanned a highly conserved 4-kb genomic region (FIG. 1). In embryonic day 14.5 (E14.5) hearts, this genomic region was enriched with chromatin signatures of active enhancers—acetylated histone 3 lysine 27 (H3K27ac) and monomethylated histone 3 lysine 4 (H3K4me1) with low levels of trimethylated histone 3 lysine 4 (H3K4me3)—and the boundaries of this genomic region were well-demarcated by levels of H3K27ac and H3K4me1 (FIG. 1). Also, this genomic region contained consensus binding motifs of transcriptional factor MEF2A and GATA4 that are critical for heart development, and the motifs were conserved between mouse and human. Accordingly, we postulated this 4-kb DNA functioned as a cardiac-specific enhancer and referred to it as eDNA. To test whether eDNA was an enhancer, we fused the eDNA fragment to basal heat shock promoter hsp68 to drive the expression of lacZ reporter gene in transgenic mice. We found that eDNA enhanced lacZ expression only in the heart but not other tissues of E11.5 embryos, indicating a cardiac-specific enhancer activity. DNAse-I footprinting studies (ENCODE database) revealed hypersensitivity sites in eDNA region primarily in the heart, consistent with its cardiac-specific activity. The role of eDNA as a cardiac-specific enhancer was collectively supported by chromatin signatures, in vivo reporter studies, DNAse-I footprinting, as well as the ability of eDNA to undergo looping to its target promoters, and its bidirectional transcription into cardiac-specific noncoding RNAs.

Given that eDNA was located upstream of Myh genes, we asked whether eDNA targeted Myh genes. We first examined Myh expression in mouse hearts lacking eDNA. To generate eDNA knockout mice, we used Clustered Regularly Interspaced Short Palindromic Repeats (CRISPR) technology to introduce two loxP sites flanking eDNA (eDNA$^{f/f}$). eDNA$^{f/f}$ alleles were then deleted in cardiomyocytes by Cre recombinase driven by Sm22α promoter, which acted in fetal cardiomyocytes by E8.5 and deleted eDNA efficiently. In E13.5 eDNA-null hearts (Sm22αCre;eDNA$^{f/f}$), Myh7 was decreased by 60%, Myh6 increased 62%, and Myh7/6 ratio reduced 75% (FIG. 2), suggesting that eDNA is active in fetal hearts to maintain high Myh7 and low Myh6 expression. We then tested whether eDNA was required for pathological Myh switch in stressed adult hearts. We crossed eDNA$^{f/f}$ with the driver Tnnt2-rtTA;TRE-Cre to enable doxycycline-inducible, cardiomyocyte-specific deletion of eDNA in adult hearts, with Cre recombinase driven by cardiac-specific troponin (Tnnt2) promoter and tetracycline response element (TRE). In this mouse line (Tnnt2-rtTA; TRE-Cre;eDNA$^{f/f}$), doxycycline treatment effectively deleted eDNA within 7 days. In normal adult hearts, eDNA deletion had no impact on Myh6 or Myh7 levels (FIG. 3), suggesting the lack of eDNA activity in mature hearts. However, when the hearts were pressure-overloaded by transaortic constriction (TAC), eDNA deletion prevented stress-induced Myh6-to-Myh7 switch and restored Myh isoform expression to pre-stress levels (FIG. 4), indicating that eDNA is active in stressed hearts to trigger pathological Myh switch, a return to fetal state. Overall, the results suggest that eDNA is functionally active in fetal and stressed hearts to control Myh isoform expression.

Figure 2:
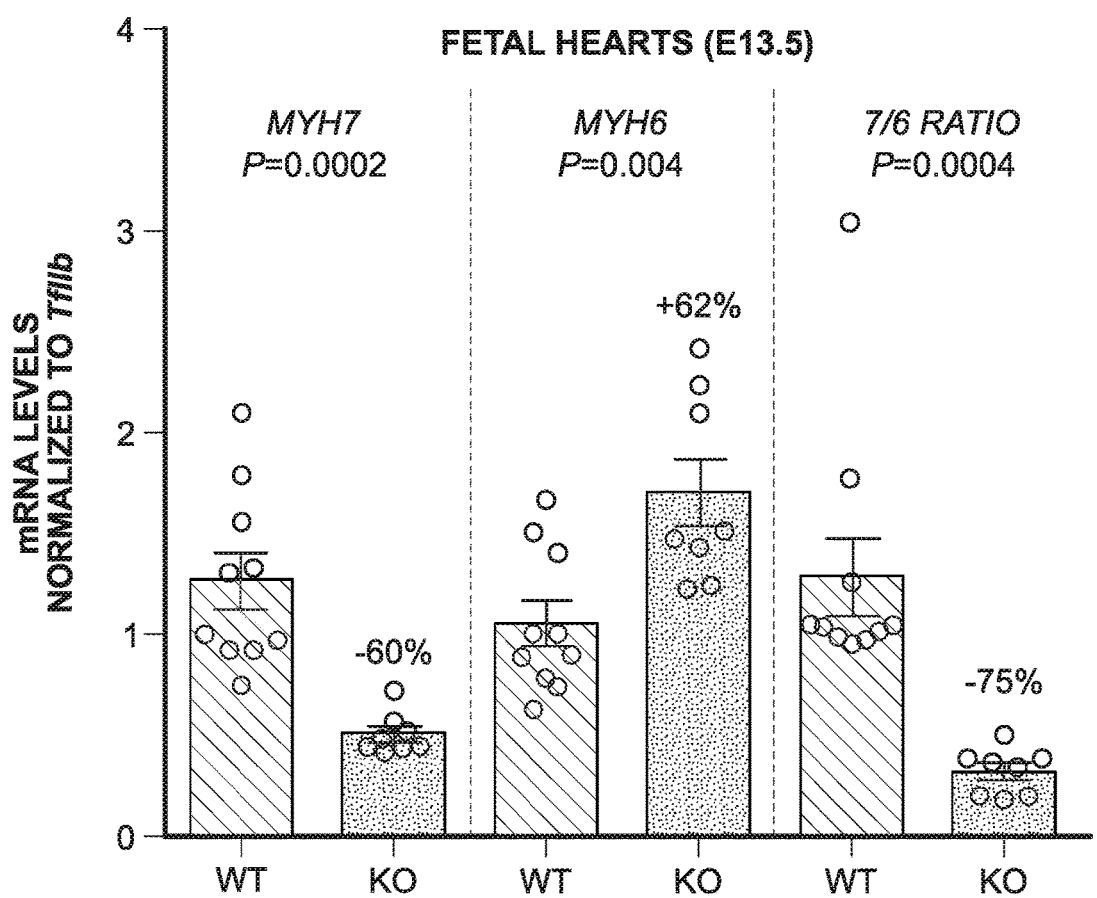
FIG. 2 is a graph representing the quantitation of Myh6 and Myh7 mRNAs in E13.5 e-DNA-null hearts (Sm22α-Cre;eDNA$^{f/f}$) verses wild type (wt) fetal hearts.
Figure 3:
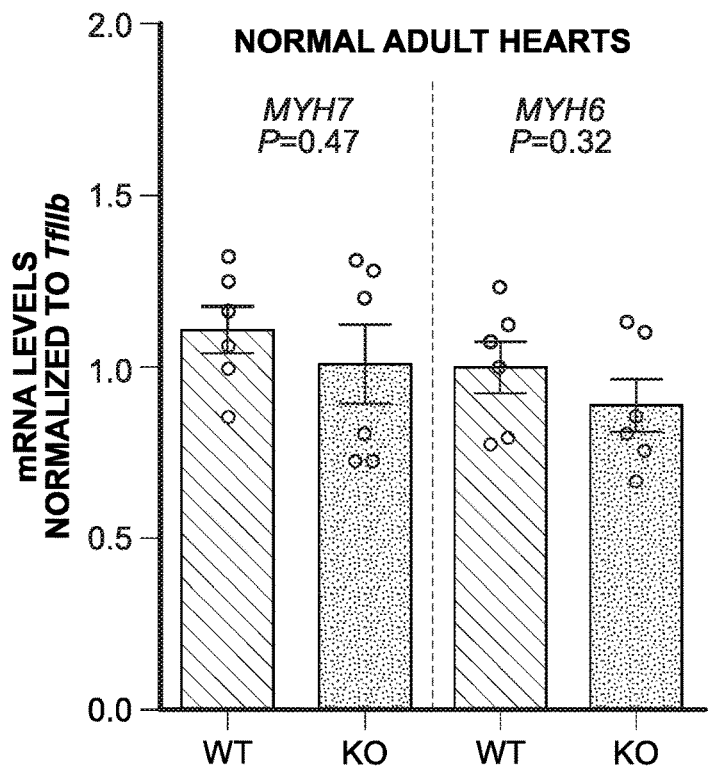
FIG. 3 is a graph representing the quantitation of Myh6 and Myh7 mRNAs in adult eDNA-null hearts (Tnnt2-rtTA; TRE-Cre;eDNA$^{f/f}$) verses wild type (wt) adult hearts.

We then tested whether eDNA could form a three-dimensional chromatin loop, like an enhancer, to its target Myh7 and Myh6 promoters (FIG. 1). We conducted chromosome conformation capture with quantitative PCR (3C-qPCR) to determine the looping between eDNA and Myh promoters. In fetal and stressed adult hearts when eDNA was essential for Myh expression (FIGS. 2 and 4), eDNA was capable of looping to Myh6 and Myh7 proximal promoters, which were previously shown to control Myh isoform expression. Conversely, eDNA displayed much diminished looping to Myh loci in normal adult hearts, consistent with its lack of activity on Myh expression in mature hearts (FIG. 3). The specificity of 3C-qPCR assays was validated by sequencing of the PCR products. Remarkably, Myh6 and Myh7 promoters, although 28-kb apart, were in close proximity in the three-dimensional chromatin space, providing a structural basis for their coordinated changes. Collectively, the results of eDNA reporter, knockout, and chromatin looping studies indicate that eDNA acts as an enhancer to control Myh promoters in fetal and stressed hearts. Next, we asked whether eDNA was essential for hypertrophy, given that Myh isoform ratio controls cardiac resistance to pathological stress. Indeed, in eDNA-null hearts (Tnnt2-rtTA;TRE-Cre;eDNA$^{f/f}$), TAC-induced hypertrophy was reduced by 55%, with the decline of left ventricular fractional shortening reduced by 42%. These studies demonstrated a pathogenic role of eDNA as an enhancer in stress-induced Myh switch and hypertrophy.

Figure 4:
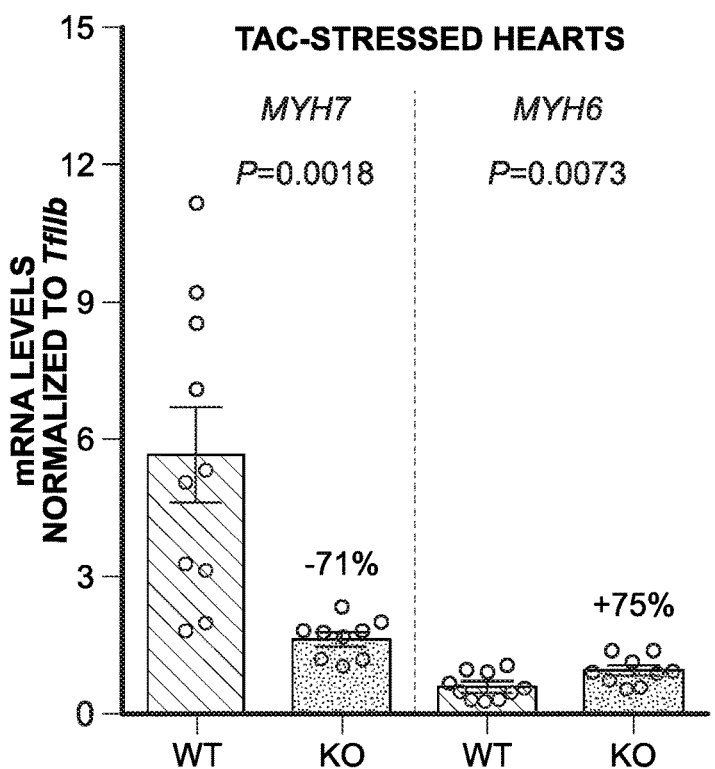
FIG. 4 is a graph representing the quantitation of Myh6 and Myh7 mRNAs in adult eDNA-null hearts or in wild type (wt) adult hearts 7 days after TAC.
Figure 5:
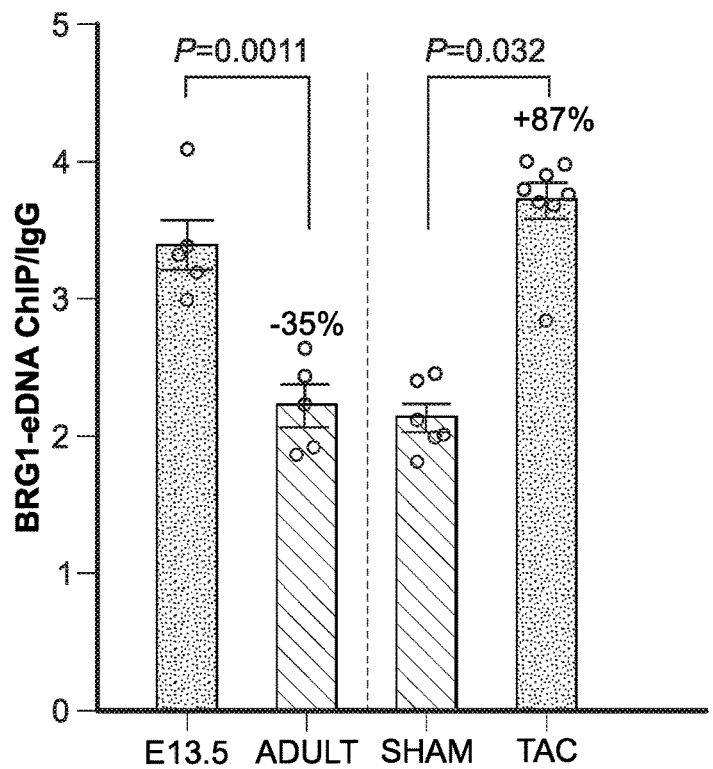
FIG. 5 is a graph representing a ChIP analysis of Brg1-eDNA binding in E13.5 hearts and adult hearts 7 days after sham or TAC operation.
Figure 6:
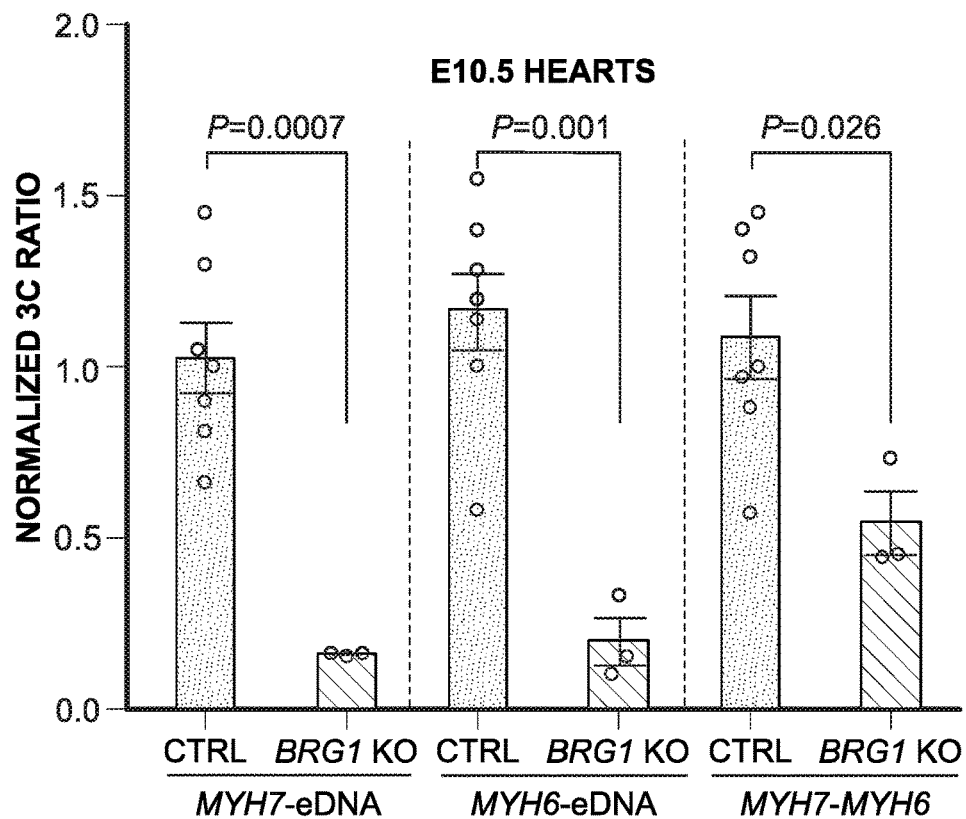
FIG. 6 is a graph representing a 3C analysis of Myh6 and Myh7 proximal promoters and eDNA in control (Ctrl) and Brg1-null hearts (KO) of E10.5 embryos.
Figure 7:
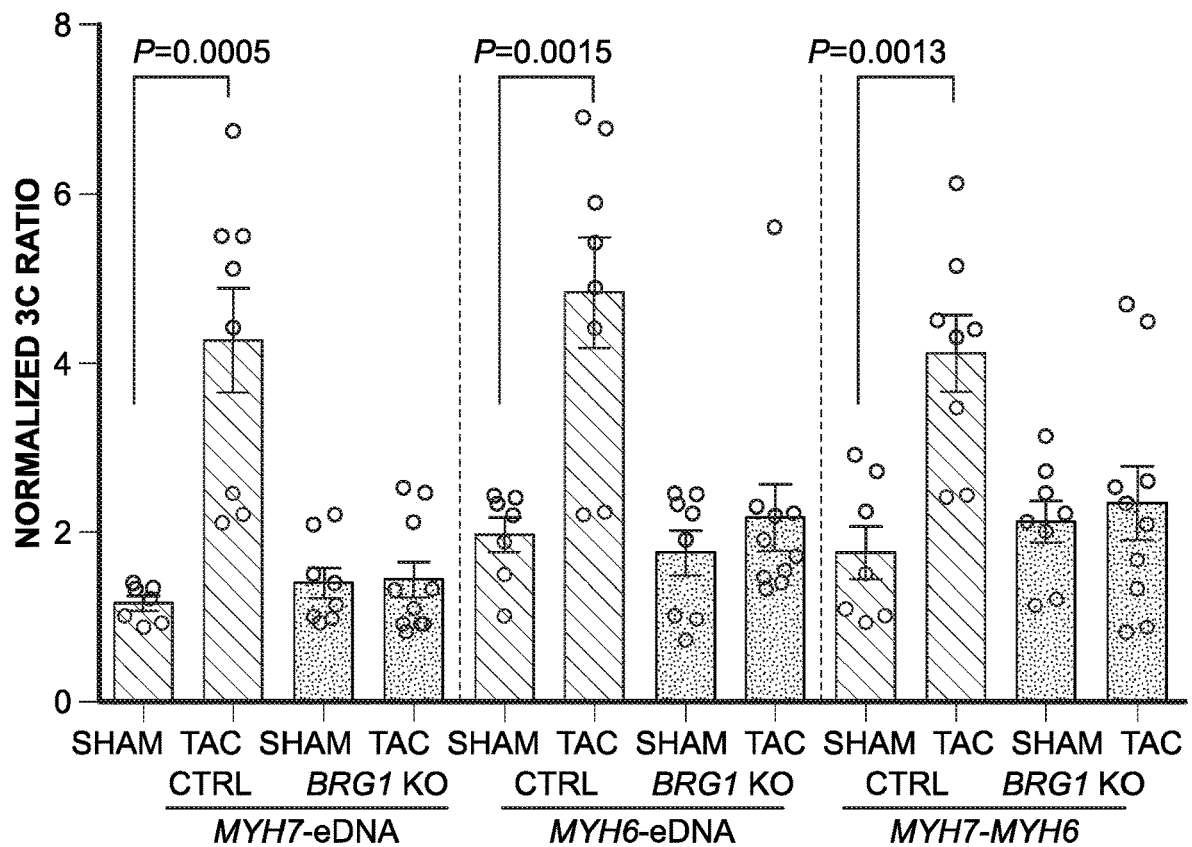
FIG. 7 is a graph representing a 3C analysis of Myh6 and Myh7 proximal promoters and eDNA in control (Ctrl) and Brg1-null hearts (KO) adult hearts 7 days after sham or TAC operation.

We next asked if Brg1, a pro-hypertrophic chromatin remodeler that triggered Myh switch, was essential for eDNA looping to Myh loci. Chromatin immunoprecipitation (ChIP) of heart tissues showed that Brg1 was enriched on eDNA in fetal hearts (E13.5), whereas its occupancy of eDNA was reduced by 35% in normal adult hearts (FIG. 5). Upon cardiac stress by TAC, Brg1 was activated and re-accumulated on eDNA with 87% increase of ChIP signals, restoring the occupancy to fetal levels (FIG. 5). The results suggested that Brg1 bound to eDNA to trigger eDNA-Myh looping and Myh switch. The functional requirement of Brg1 was revealed by the disruption of eDNA-Myh looping in fetal or stressed hearts lacking myocardial Brg1 (Sm22α-Cre;Brg1$^{fl/fl}$ or Tnnt2-rtTA;TRE-Cre;Brg1$^{f/f}$) (FIGS. 6 and 7). Brg1 and eDNA knockout studies showed that both Brg1 and eDNA were essential for eDNA-Myh looping to trigger Myh switch in response to pathophysiological stimuli (FIGS. 2, 3, 4). The formation or disruption of a Brg1-eDNA-Myh6-Myh7 three-dimensional complex provides a critical spatial mechanism to orchestrate antithetical Myh changes.

We asked whether eDNA activity was regulated by its transcription into RNAs. By 5' and 3' rapid amplification of cDNA ends (RACE) analysis of adult mouse hearts, we identified two RNA species transcribed from the 4-kb eDNA region. A 3.3-kb RNA was transcribed in an opposite direction from Myh7 gene, and the other 0.75-kb RNA (Anti-sense-eRNA) in Myh7 direction. In adult hearts, both RNA species were detectable by northern blot analysis, confirming their length identified by RACE.

We then focused on the 3.3-kb RNA to study its pathophysiological role and named this eRNA Uheart (abbreviated as Uhrt) for Upstream Myosin Heavy Chain RNA Transcript. Strand-specific RT-qPCR showed Uhrt levels were minimal in embryonic hearts (FIG. 8), when eDNA was enriched with chromatin signatures of activity (H3K27ac and H3K4m1) and underwent looping to Myh promoters to activate Myh7 isoform (FIGS. 1 and 2). Conversely, as Uhrt expression increased from fetal to neonatal and to adult phase (FIG. 8), chromatin signatures of eDNA activity (H3K4m1 and H3K27ac) diminished, along with physiological Myh switch and reduced eDNA-Myh looping. Remarkably, Uhrt increased sharply within the first 24 hours after birth, while Myh7 levels dropped precipitously in the same period, indicating an abrupt neonatal cessation of eDNA-Myh looping. Therefore, Uhrt can be transcribed from eDNA only when eDNA is functionally silent with minimal looping to its target Myh promoters. This contrasts sharply with known eRNAs, whose levels of expression track activities of enhancers and promoters. The Uhrt-eDNA interaction suggests a new mode of eRNA function.

Uhrt was expressed specifically in the heart: its levels were undetectable or minimal in non-cardiac tissues. In adult hearts Uhrt was transcribed in cardiomyocytes but not endothelial cells or fibroblasts and was highly enriched in the nuclei, revealed by cell sorting and nuclear/cytoplasmic fractionation studies. Codon substitution frequency suggested a highly negative translation score of Uhrt (−1148), which was further confirmed by in vitro transcription and translation of Uhrt that found no peptide translation. Ribosome profiling of adult hearts showed minimal ribosome binding to Uhrt, consistent with Uhrt being a nuclear, noncoding RNA. These observations together demonstrated that Uhrt is a cardiomyocyte-specific enhancer RNA transcribed from a functionally inactive enhancer in mature hearts.

Figure 9:
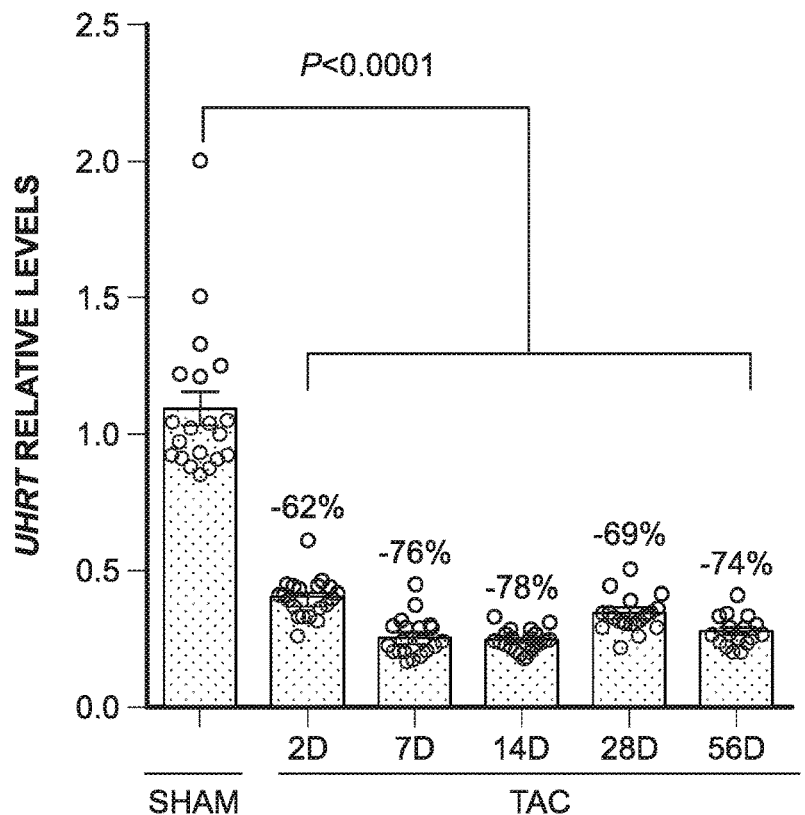
FIG. 9 is a graph representing the quantification of cardiac Uhrt RNAs 2-56 days (d) after TAC operation.
Figure 10:
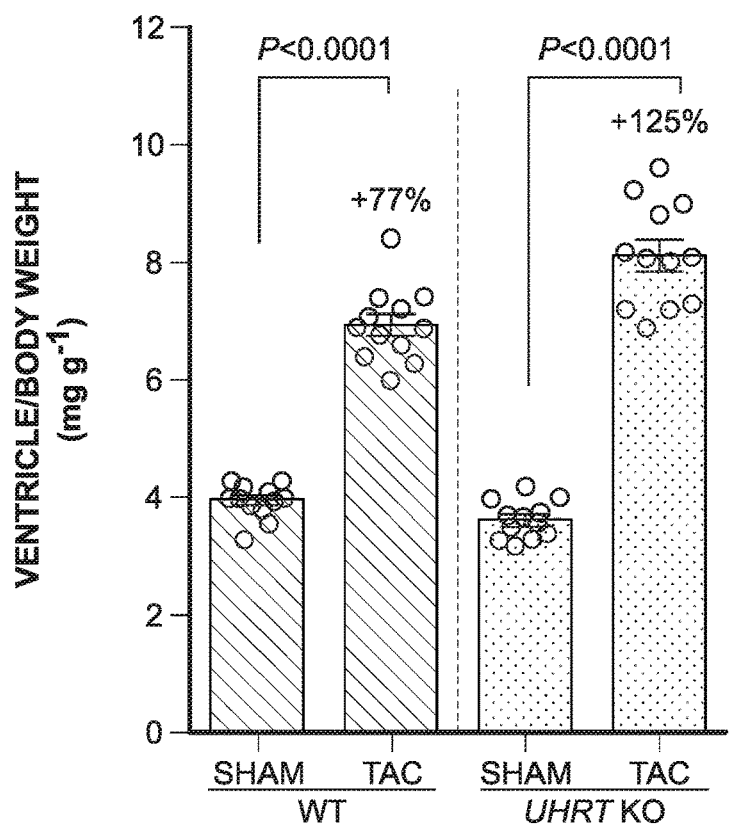
FIG. 10 is a graph representing the ventricle/body-weight ratio of hearts 2 weeks (w) after TAC.
Figure 11:
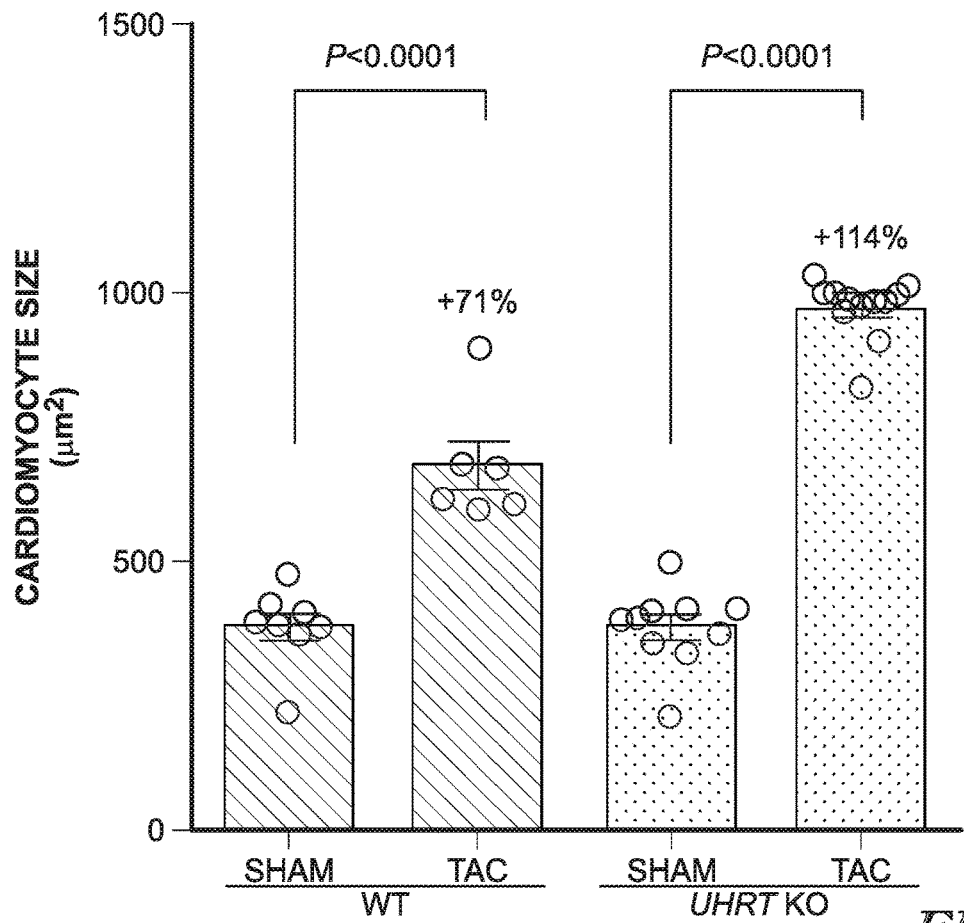
FIG. 11 is a graph representing the quantification of cardiomyocyte cross-sectional areas by wheat germ agglutinin staining in WT and Uhrt KO mice 2 weeks after TAC.

We predicted that Uhrt transcription would be compromised in TAC-stressed hearts where eDNA displayed enhancer activity and Myh looping. Indeed, strand-specific RT-qPCR of heart tissues showed that Uhrt expression was reduced by 62% within 2 days after TAC, and its levels remained reduced by 62-78% in 7-56 days after TAC (FIG. 9), suggesting a role of Uhrt in pathological hypertrophy. To assess its in vivo function, we used CRISPR to insert upstream of Uhrt a red fluorescent protein variant (tdTomato) followed by 3 repeats of polyA transcription termination signals (tdTO3×polyA) to stop Uhrt, transcription. This genetic knockout was specific to Uhrt since it didn't affect Antisense-eRNA transcription from the same eDNA nor did it alter eDNA-dependent Myh6 and Myh7 expression in E13.5 hearts that had minimal Uhrt transcription. The Uhrt-null mice lived to adulthood and appeared grossly normal with normal weight, body size, and left ventricular fractional shortening. The lack of Uhrt in adult hearts, however, accelerated cardiac functional decline caused by TAC. Within 2 weeks of TAC, factional shortening of Uhrt-null hearts decreased from 40% to 18%, whereas the control showed a decline from 40% to 30%, showing a 40% excess of functional decline in the absence of Uhrt. After 12 weeks of TAC, Uhrt-null mice had a mortality of 90%, while control mice 25%, revealing a 3.6-fold excess of mortality. Also, Uhrt-null hearts exhibited 114-125% increase of hypertrophy by ventricle/body-weight ratio and by cardiomyocyte cross-sectional area, compared to 71-77% increase of hypertrophy in control hearts (FIGS. 10 and 11), indicating 1.6-fold excess hypertrophy. Uhrt-null hearts are therefore susceptible to stress-induced pathology, suggesting a cardioprotective role of Uhrt, opposite to that of eDNA.

Figure 12:
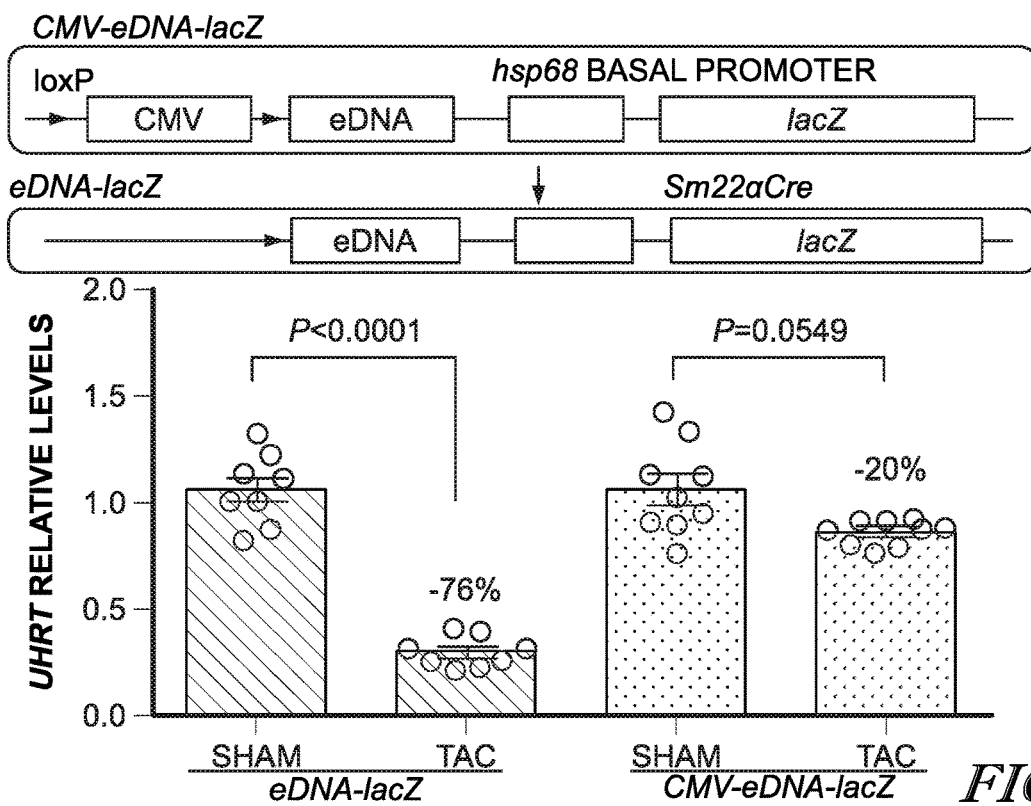
FIG. 12 is an illustration of eDNA reporter mouse lines and quantification of Uhrt 7 days after sham or TAC operation.
Figure 13:
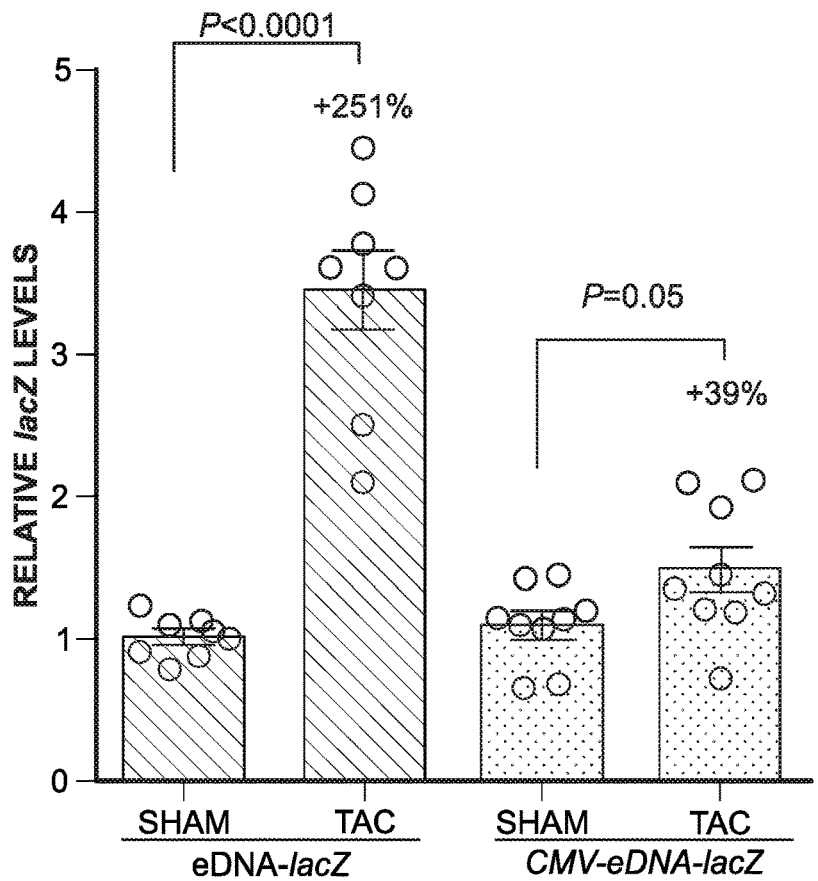
FIG. 13 is a graph representing the quantification of lacZ RNAs in hearts from eDNA reporter mice 7 days after sham or TAC operation.

To address whether Uhrt transcription blocked eDNA activity in the heart, we generated a stable transgenic reporter mouse line in which Uhrt transcription from eDNA was driven by a loxP-floxed CMV promoter, followed by hsp68 basal promoter fused to lacZ reporter (CMV$^{flox}$-eDNA-hsp68-lacZ abbreviated as CMV-eDNA-lacZ) (FIG. 12). The CMV promoter, whose activity wasn't inhibited by TAC, allowed Uhrt expression under stress conditions to rescue Uhrt levels in TAC-stressed hearts. Conversely, transgenic Uhrt expression could be shut down by Sm22α-Cre that removed the floxed CMV promoter but maintained eDNA in Sm22α-Cre;CMV$^{flox}$-eDNA-hsp68-lacZ line (abbreviated as eDNA-lacZ). In TAC-stressed hearts, where endogenous Uhrt was repressed, CMV-eDNA-lacZ transcribed Uhrt 3.2-fold higher than eDNA-lacZ mice (FIG. 12), showing a rescue of Uhrt levels by CMV promoter. The CMV-eDNA-lacZ line with high Uhrt expression displayed low eDNA activity on hsp68 promoter, whereas eDNA-lacZ line that had 3-fold less Uhrt showed 6.4-fold stronger eDNA activity (FIG. 13). The rescue of Uhrt by CMV promoter was therefore sufficient to eliminate TAC-induced eDNA activity (FIG. 13). Conversely, in sham-operated or normal adult hearts, which had abundant endogenous Uhrt and minimal Brg1 that's required for eDNA activity, both transgenic reporter lines showed low eDNA activity (FIG. 13). These in vivo reporter studies indicate that Uhrt inhibits eDNA activity on target promoters.

Figure 8:
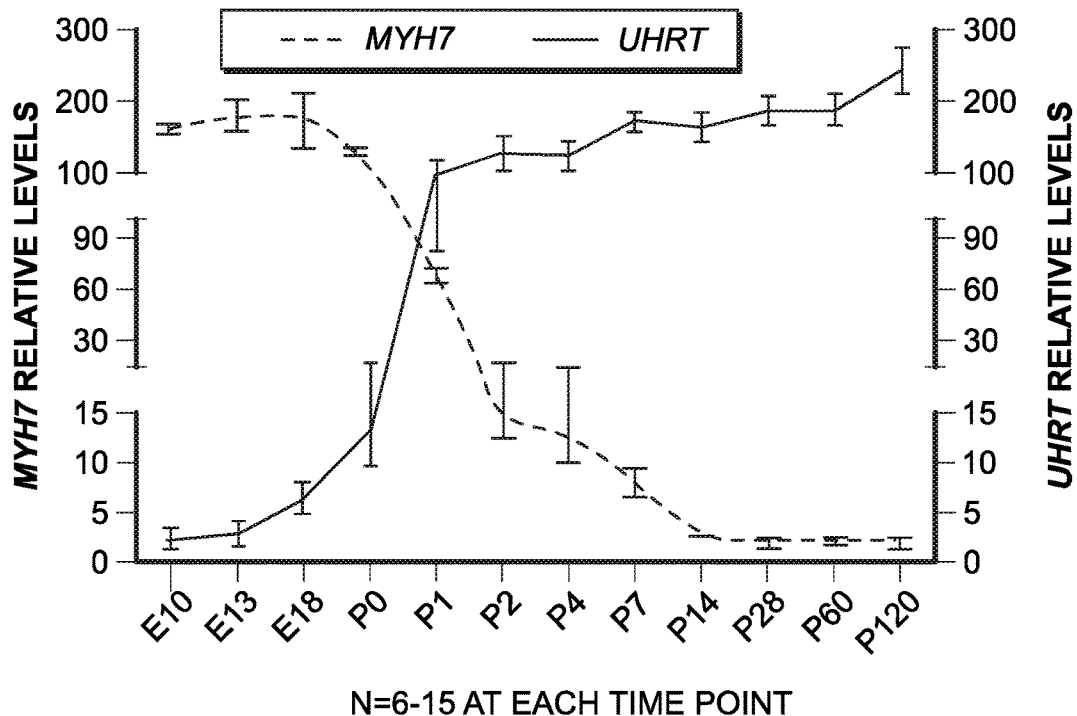
FIG. 8 is a graph representing the quantitation of Uhrt and Myh7 RNA in mouse hearts. P: postnatal day.

We then set out to find how Uhrt inhibited eDNA activity. We postulated that Uhrt might hybridize with its eDNA template to form RNA-DNA hybrid duplex with a unpaired, non-template strand of eDNA—a triplex R loop structure that might prohibit eDNA looping. To test this model, we first examined the distribution of nuclear Uhrt between chromatin and nucleoplasm. By strand-specific RT-qPCR and chromatin-nucleoplasm fractionation, we found that 25% of Uhrt transcripts existed in the nucleoplasm (nuclei depleted of chromatin), and 75% of Uhrt were associated with chromatin, indicating that most Uhrt was tethered to chromatin. To test whether Uhrt bound to eDNA to form RNA-DNA hybrid, we used the antibody S9.6 that specifically detects RNA-DNA hybrid duplex to conduct DNA-RNA hybrid immunoprecipitation (DRIP) followed by strand-specific RT-qPCR to quantitate Uhrt. In E13.5 hearts, we found no enrichment of Uhrt in the RNA-DNA hybrid, consistent with low Uhrt levels in embryos (FIG. 8). Conversely, in mature adult hearts, DRIP-qPCR showed that Uhrt was enriched by 3.7-4.2-fold in the RNA-DNA hybrid complex, the formation of which, however, was suppressed by TAC. The specificity of RNA-DNA hybrid was confirmed by Rnase H, which specifically degrades RNA-DNA hybrid. Therefore, Uhrt predominantly existed in RNA-DNA form tethered to eDNA.

These results were further supported by the guanine over cytosine (GC) skew score of Uhrt, which measures (G−C)/(G+C) ratio in RNA to predict RNA-DNA hybrid formation. The 5' 1.1-kb of Uhrt, which had the lowest score of GC skew score (0.029), exhibited the lowest RNA-DNA enrichment by DRIP, whereas the mid-third 1.1-kb and 3'-third 1.1-kb fragments of Uhrt, which had much higher GC skew score (0.16), displayed the highest DRIP enrichment. Therefore, the 3' 2.2-kb fragment of Uhrt was tethered to eDNA as an RNA-DNA hybrid duplex. We then tested the presence of an unpaired, non-template strand eDNA in the R-loop triplex. Single-strand DNAs (ssDNAs) are known to be coated by a ssDNA-specific binding protein-replication protein A (RPA). By chromatin-IP using antibodies against RPA coupled with qPCR, we found that RPA-eDNA complex increased by 171% in adult hearts with abundant Uhrt-eDNA hybrid, compared to that of E13.5 hearts that had minimal Uhrt-eDNA hybrid. In TAC-stressed hearts, as expected, the RPA-eDNA complex was reduced by 42%, along with a reduction of Uhrt-eDNA hybrid. Overall, these observations demonstrated that Uhrt hybridizes with eDNA to form a triplex R loop structure, consisting of a Uhrt-eDNA hybrid duplex with an unpaired strand of eDNA.

We next asked whether Brg1 or its associated factor could bind to Uhrt-eDNA hybrid. We first investigated the role in eDNA looping of CCCTC-binding factor (CTCF), a regulator protein essential for chromatin looping and three-dimensional structure formation. CTCF contains 11 highly conserved zinc finger domains, capable of binding to specific double-stranded DNA sequence to cause chromatin looping. We found a CTCF consensus binding motif (AGGGGGTGG; SEQ ID NO: 43) on eDNA near the conserved MEF2A and GATA4 sites. ChIP analysis of heart tissues verified CTCF was enriched on eDNA region in E13.5 hearts, whereas its occupancy on eDNA dropped by 42% in normal adult hearts, but was increased by 81% and restored to fetal levels by TAC, while CTCF protein levels remained unchanged. Such dynamic CTCF binding to eDNA coincided with and accounted for the ability of eDNA to loop to Myh loci in fetal and stressed hearts. Interestingly, the CTCF binding site on eDNA was guanine-rich with a GC skew score of 0.66, which was highly prone to form RNA-DNA hybrid, and indeed, this site resided within the Uhrt-eDNA hybrid zone. Given that CTCF contains zinc finger domains that bind to DNA duplex, we hypothesized that CTCF binding to eDNA was disabled by the formation of Uhrt-eDNA hybrid across the binding site. Using electrophoretic mobility shift assay (EMSA) and probes of CTCF binding site sequence, we found that CTCF proteins were capable of binding to the double-stranded eDNA binding site, but failed to bind Uhrt-eDNA duplex in this binding site. Mutation of the double-stranded eDNA probe (AGGGGGTGG (SEQ ID NO: 43) to AAAAAATGG (SEQ ID NO: 44)) disrupted CTCF binding in EMSA, indicating a specificity of the binding site. The in vivo ChIP and in vitro EMSA studies, together, revealed the ability of Uhrt to inhibit CTCF binding to eDNA, thus preventing eDNA looping.

Figure 14:
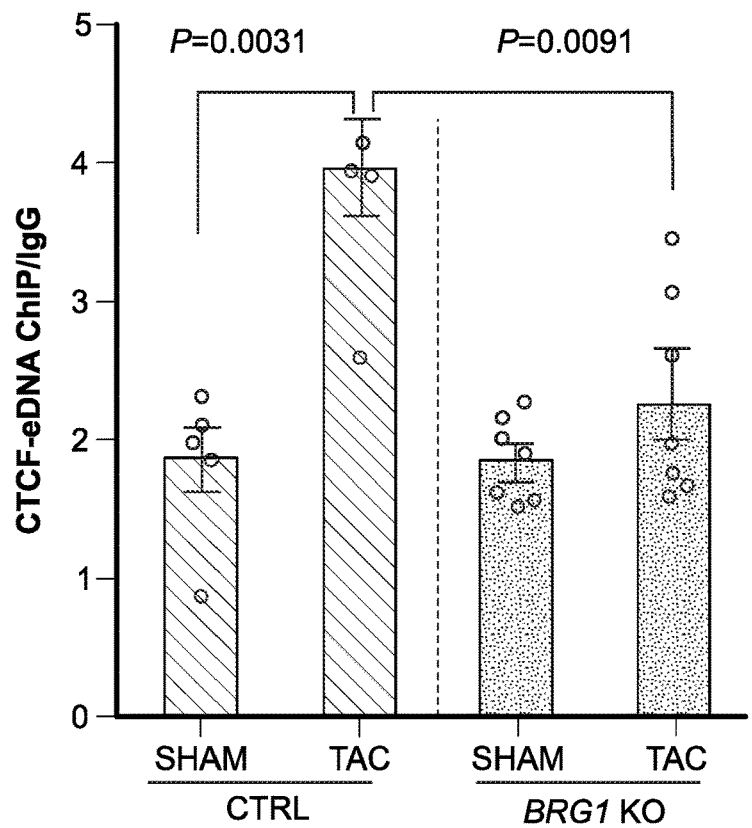
FIG. 14 is a graph representing a ChIP quantitation of CTCF-eDNA binding in adult control (Ctrl) and Brg1-null (KO) hearts 7 days after sham or TAC operation.
Figure 15:
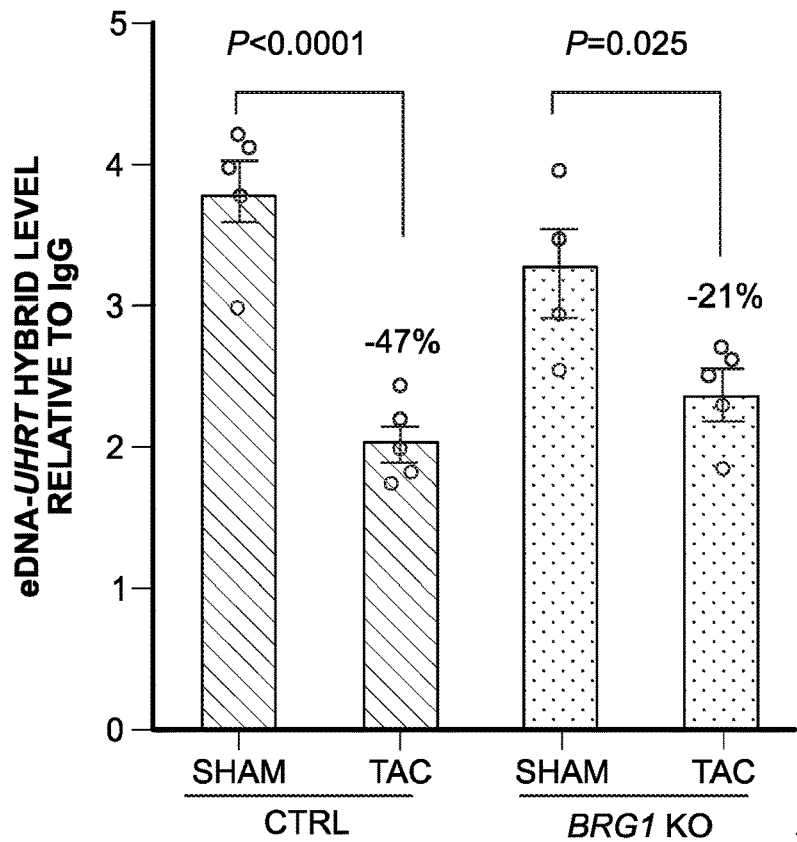
FIG. 15 is a graph representing a DRIP quantitation of Uhrt-eDNA hybrid in control (Ctrl) and Brg1-null (KO) adult hearts 2 days after sham or TAC operation.

Given that Brg1 was essential for eDNA looping, we tested whether CTCF was recruited by Brg1 to eDNA to trigger the looping. Indeed, loss of Brg1 abolished CTCF binding to eDNA in TAC-stressed hearts of Tnnt2-rtTA; TRE-Cre;Brg1$^{f/f}$ mice (FIG. 14). The ability of CTCF to bind eDNA duplex but not Uhrt-eDNA hybrid brought the next question: how did Brg1 resolve Uhrt-eDNA hybrid and restore eDNA duplex to enable CTCF binding? DRIP-qPCR analysis of heart tissues showed that in the absence of myocardial Brg1 (Tnnt2-rtTA;TRE-Cre;Brg1$^{f/f}$), Uhrt-eDNA hybrid was restored by 60% in TAC-stressed hearts (FIG. 15), suggesting that Brg1 was essential for disrupting Uhrt-eDNA hybrid. The persistence of Uhrt-eDNA hybrid in Brg1-null hearts, however, wasn't caused by increased Uhrt levels in stressed Brg1-null hearts. Therefore, in stressed hearts, there were two factors that contributed to the resolution of Uhrt-eDNA hybrid structure—the reduction of Uhrt transcription and the activation of Brg1 to resolve that structure.

Figure 16:
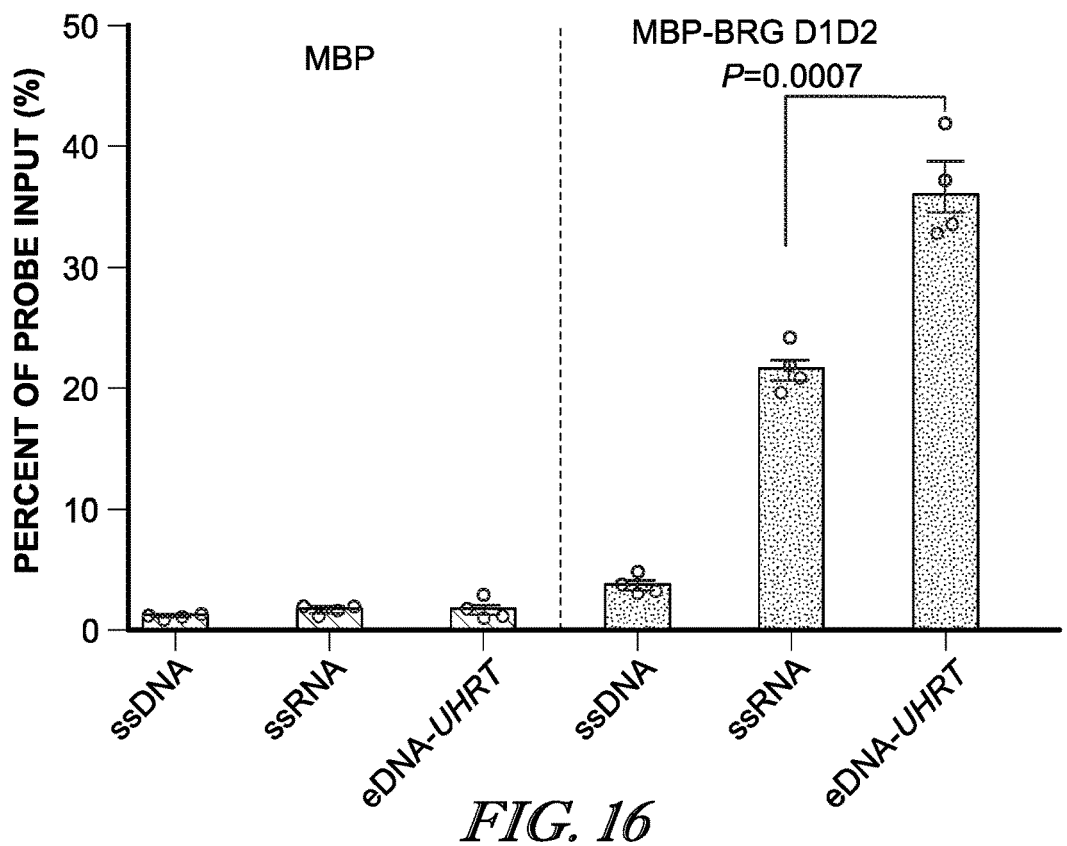
FIG. 16 is a graph representing an, amylose pull-down assay of MBP-Brg1 D1D2 protein binding to ssDNA (CTCF site), ssRNA (Uhrt sequence at CTCF site) and Uhrt-eDNA hybrid at CTCF site. MBP: maltose binding protein.
Figure 17:
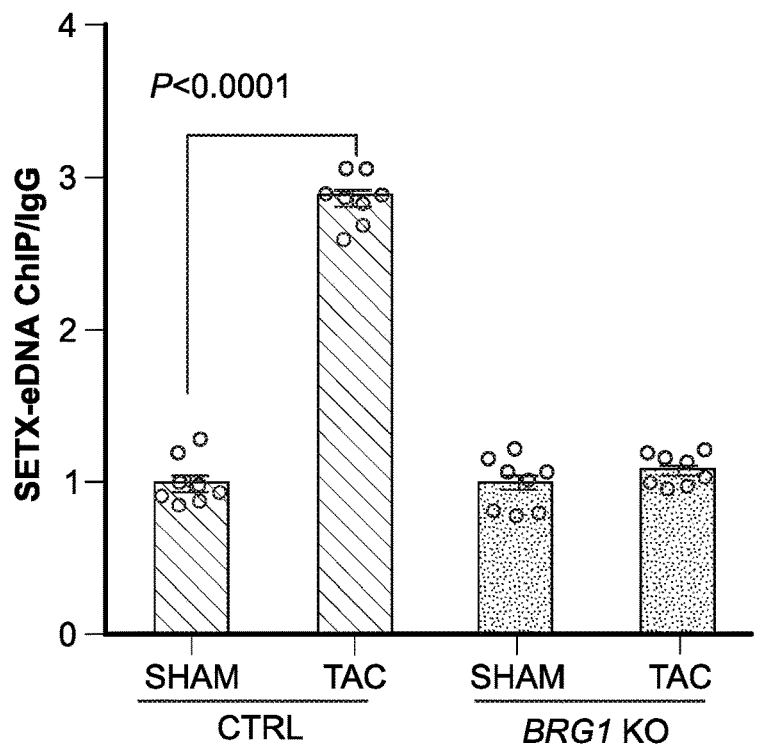
FIG. 17 is a graph representing a ChIP analysis of Setx-eDNA binding in adult Ctrl and Brg1-null (KO) hearts 7 days after sham or TAC operation.
Figure 18:
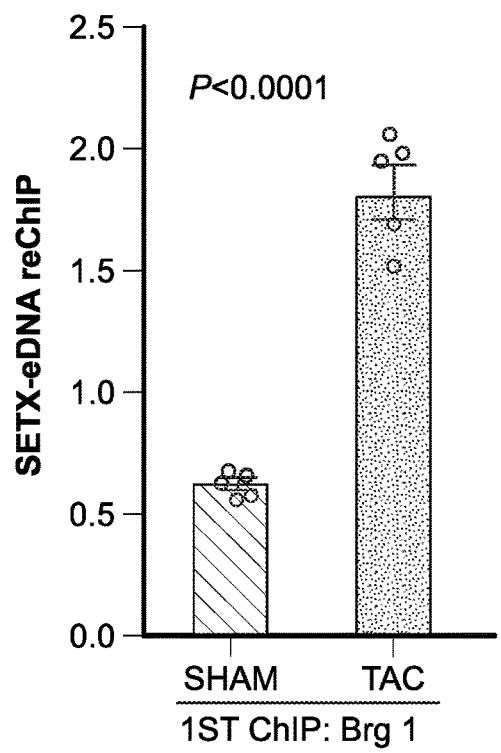
FIG. 18 is a graph representing a ChIP-on-ChIP quantitation of Setx on Brg1-immunoprecipitated eDNA 7 days after sham or TAC operation.

To test how Brg1 could disrupt Uhrt-eDNA hybrid, we first used amylose pulldown experiments to examine Brg1's binding to the following probes: ssDNA (CTCF binding site), ssRNA (Uhrt sequence at CTCF binding site), and Uhrt-eDNA hybrid (CTCF binding site). We found that Brg1 couldn't bind ssDNA, bound ssRNA modestly, but bound Uhrt-eDNA hybrid strongly (FIG. 16). Brg1, unlike CTCF, was capable of binding Uhrt-eDNA hybrid. To further determine how Brg1 resolved Uhrt-eDNA hybrid, we examined Brg1's interaction with Senataxin (Setx), a major RNA-DNA hybrid helicase that's known to resolve RNA-DNA hybrid in vivo. By ChIP analysis, we found that Setx occupied eDNA in TAC-stressed hearts when Brg1 was up-regulated, with 3-fold enrichment compared to normal hearts that had low Brg1 expression (FIG. 17). Such stress-induced Setx binding to eDNA was abolished by myocardial Brg1 knockout (Tnnt2-rtTA;TRE-Cre;Brg1$^{f/f}$) in which Setx proteins levels remained unchanged (FIG. 17). Therefore, Brg1 was essential for recruiting Setx to eDNA. This recruitment was further supported by ChIP-on-ChIP analyses that showed co-occupancy of Brg1 and Setx on eDNA of TAC-stressed hearts (FIG. 18). Given the known role of Setx helicase in resolving enhancer RNA-DNA hybrids, these findings indicate that Brg1 recruits Setx to Uhrt-eDNA site to unwind the RNA-DNA hybrid, releasing eDNA strands to form DNA duplex, to enable CTCF binding and the trigger of eDNA-Myh looping and Myh isoform switch.

To determine the conservation of eDNA and Uhrt in human hearts, we searched ENCODE cardiac chromatin modifications and VISTA enhancer database. In human fetal hearts, 6-kb upstream of MYH7 transcriptional start site existed a 5.5-kb genomic region that was highly enriched with H3K27ac, a chromatin signature of active enhancers. Sequence alignment showed 50% of homology between this 5.5-kb fragment (termed heDNA) and mouse eDNA. To test heDNA enhancer activity, we generated a mouse line transgenic for heDNA-hsp68-lacZ reporter. The heDNA, indeed, displayed cardiac-specific enhancer activity on hsp68 promoter in mouse embryos, and such cardiac specificity was consistent with human chromatin studies that showed higher H3K27ac signals in hearts but minimal H3K27ac in aortic tissues. Overall, the results suggest that heDNA is the human homolog of mouse eDNA. We next tested whether heDNA was transcribed into an Uhrt homolog by 5' and 3' RACE analysis of adult human hearts. We identified a single 2.3-kb RNA species transcribed from heDNA in an opposite direction from MYH7 gene, with 57% sequence homology and similar predicted secondary structure to mouse Uhrt. Strand-specific RT-qPCR showed that this human RNA was predominantly expressed in the heart. This human RNA had highly negative coding potential score (−993), and showed no translation of peptides or proteins by in vitro translation assay, consistent of its being a noncoding RNA. These observations together suggest that this enhancer RNA is human UHRT.

Figure 19:
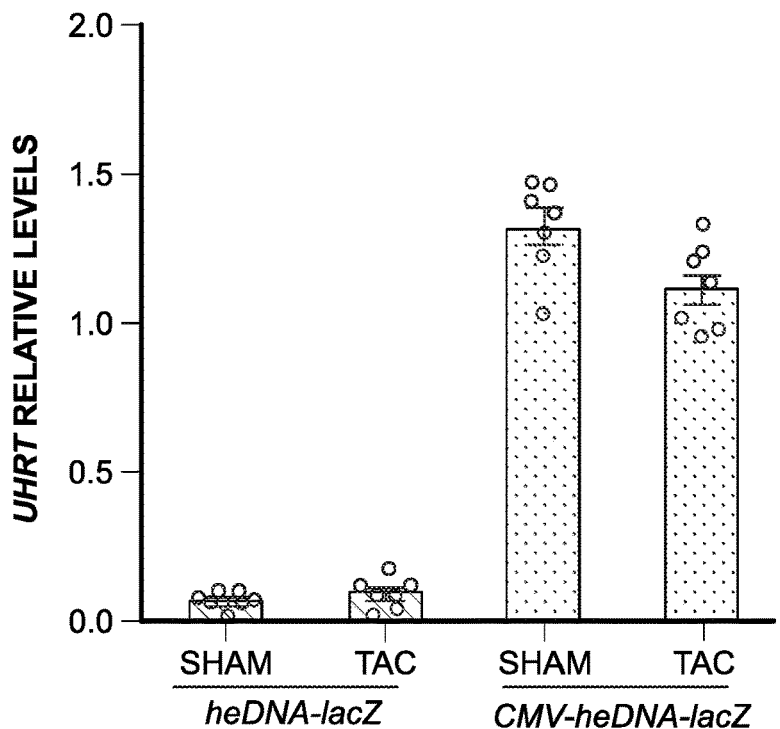
FIG. 19 is a graph representing the human Uhrt levels using an X-Gal assay with heart sections.
Figure 20:
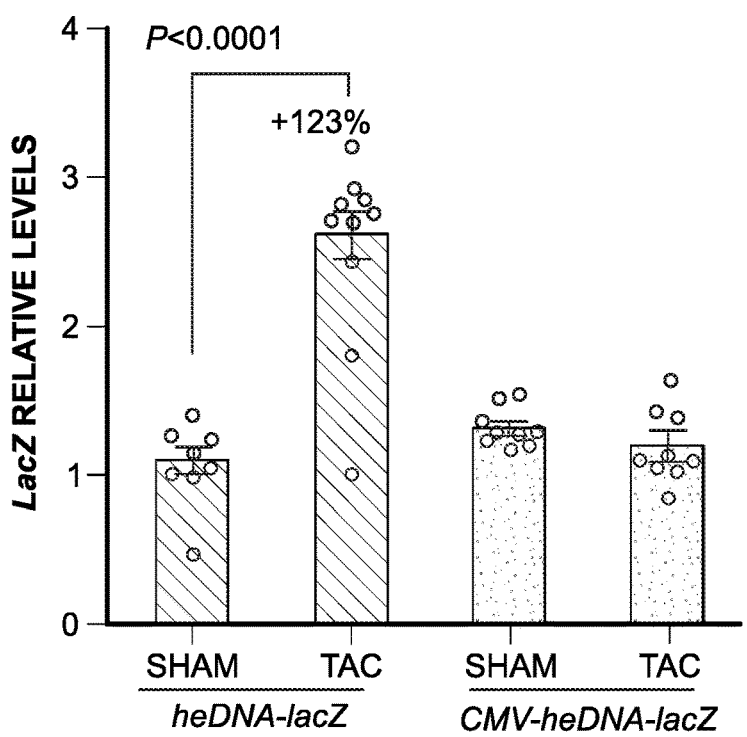
FIG. 20 is a graph representing the human Uhrt levels in heDNA reporter mice 7 days after sham or TAC operation.

To test heDNA-UHRT interaction, we generated a stable transgenic mouse reporter line in which the transcription of human UHRT from heDNA was driven by a floxed CMV promoter, followed by hsp68 basal promoter fused to lacZ reporter (CMV$^{flox}$-heDNA-hsp68-lacZ, abbreviated as CMV-heDNA-lacZ). To stop UHRT transcription, we used Sm22α-Cre to delete floxed CMV promoter in cardiomyocytes of Sm22α-Cre;CMV$^{flox}$-heDNA-hsp68-lacZ (heDNA-lacZ) mice (FIG. 19). We found that lacZ activity was induced by TAC (2.3-fold) in heDNA-lacZ hearts (without UHRT expression) but was eliminated by UHRT expression in CMV-heDNA-lacZ hearts (FIG. 20). In sham hearts, lacZ activity was minimal in either reporter mice (FIG. 20) due to the lack in normal adult hearts of Brg1 required for enhancer activity. The in vivo interaction of human eDNA and UHRT in mice indicates a mechanistic conservation of eDNA-Uhrt interaction in humans.

Figure 21:
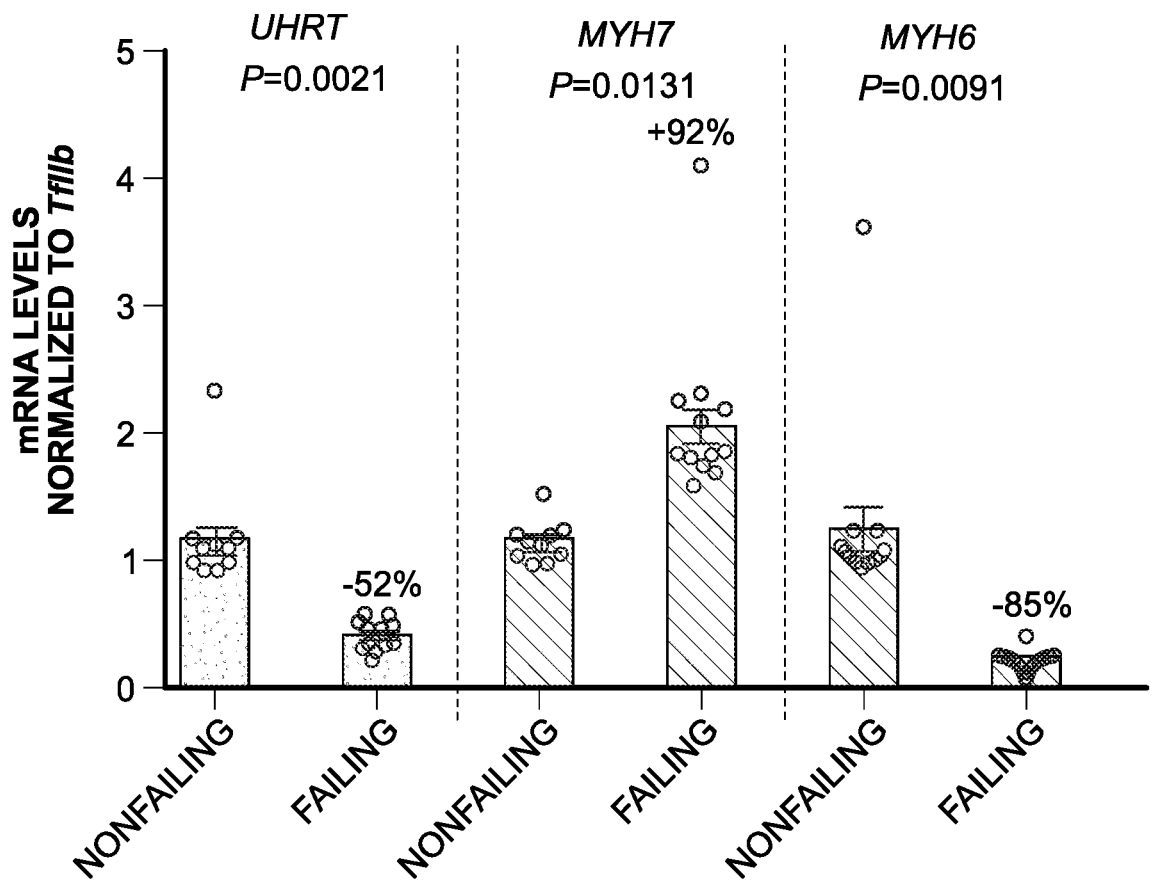
FIG. 21 is a graph representing the quantification of Uhrt, Myh6 and Myh7 RNAs of human ventricular tissues with nonfailing and failing hearts.

We then asked whether human heDNA and UHRT showed antithetical changes in human hearts, like their mouse homologs. Chromatin studies of human tissues (VISTA database) showed that heDNA contained high H3K27ac signals in the hearts with dilated cardiomyopathy compared to normal hearts, suggesting an increased heDNA enhancer activity in diseased state, similar to that of mouse eDNA in TAC-stressed hearts. Also, human UHRT expression was reduced by 52% in failing human hearts that had hypertrophic or dilated cardiomyopathy, accompanied by antithetical MYH isoform changes (92% increase of MYH7 and 85% reduction of MYH6) (FIG. 21). Such inverse correlation of heDNA activity and UHRT levels suggests an evolutionary conservation of eDNA-Uhrt interaction pertinent to the pathogenesis of human heart failure.

Figure 22:
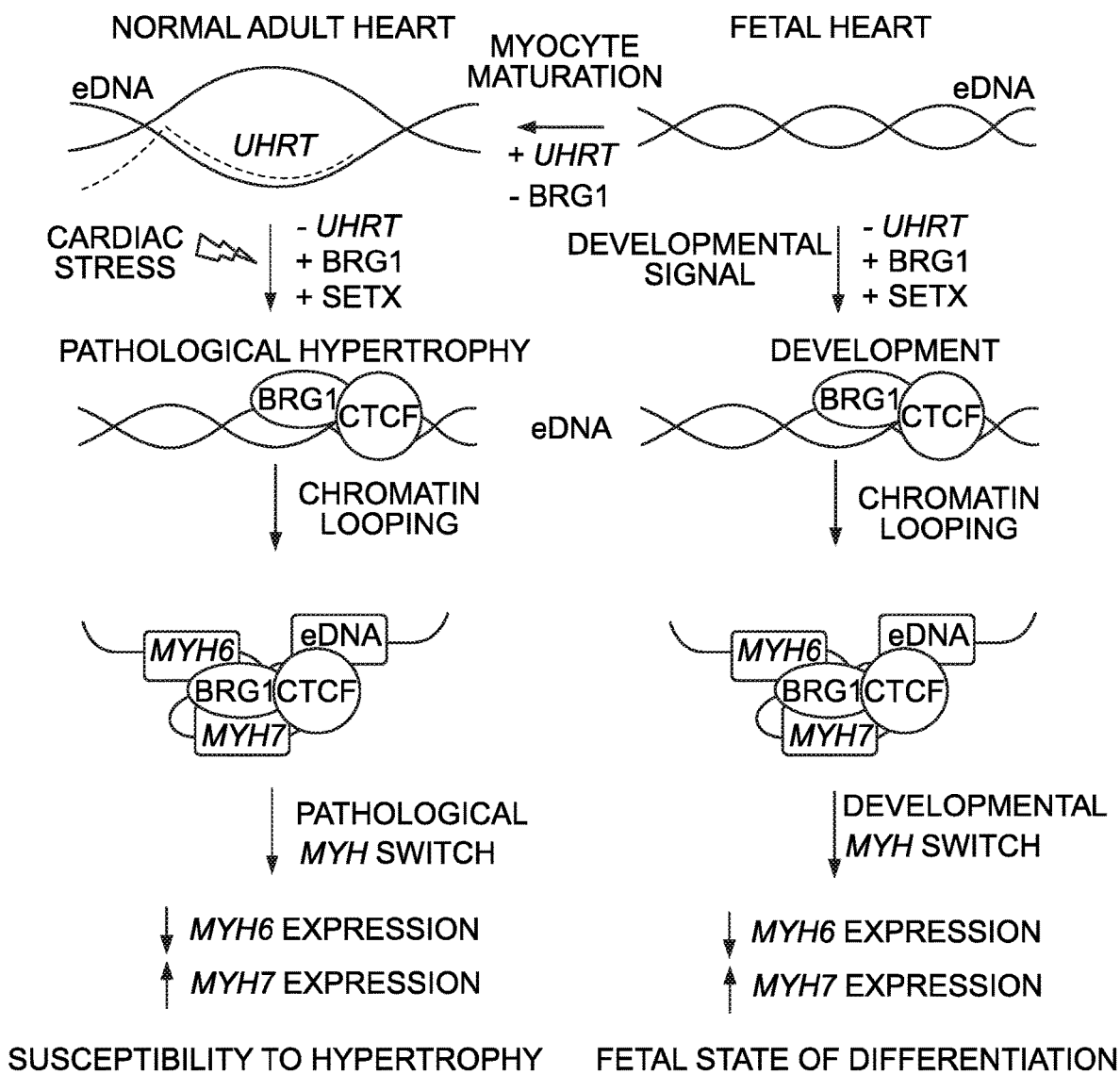
FIG. 22 is an illustration of the molecular interactions between Brg1, Uhrt, and eDNA in cardiac physiology and pathology.

Uhrt-eDNA interaction controls the assembly of eDNA-Myh6-Myh7 complex to direct antithetical Myh regulation in development and in disease to govern cardiac contractility and resistance to pathological stress (FIG. 22). Those three DNA regulatory elements (eDNA, Myh6, Myh7 promoters) are brought together in the three-dimensional space by Brg1 and CTCF to coordinate Myh regulation and cardiac pathophysiology, a process opposed by Uhrt (FIG. 22). Uhrt, like many eRNAs, arises from a bidirectionally transcribed enhancer, doesn't splice into isoforms, and maintains enhancer-encoded nucleotides for its function. These eRNA features contrast with the known enhancer-associated long noncoding RNAs (lncRNAs) expressed in the heart or fibroblasts for heart development and fibrosis. In those lncRNAs (Upperhand, WISPER, CARMEN), the enhancer-encoded nucleotides are deleted from primary RNAs, which splice into different isoforms. Uhrt thus provides a unique example of a cardiomyocyte-specific and protective eRNA, distinct from those and other lncRNAs that affect heart development or function. Using Uhrt to silence pathogenic eDNA may provide therapeutic benefits to heart failure patients. Also, identifying cardiac-specific factors essential for eDNA-Myh looping will have translational values, especially for patients with Myh7 mutations causing hypertrophic or dilated cardiomyopathy. Inhibition of such factors by small molecules can disrupt eDNA-Myh looping and shut down mutant Myh7 expression to prevent disease progression. Transcription of eRNAs is thought to reflect enhancer activation, with many eRNAs known to facilitate interactions between enhancers and promoters. However, Uhrt provides a counter example—it is transcribed by an inactive enhancer and physically blocks enhancer activation and looping toward target promoters. Transcription of eRNAs could therefore mark an inactive, rather than active, state of the enhancer. This unusual function of Uhrt reveals a new enhancer-eRNA interface in transcriptional circuitry and uncovers a new mechanism of enhancer activation, mediated by a chromatin remodeler Brg1 that recruits an RNA-DNA helicase Setx to unwind eDNA-Uhrt and enable looping. Such Brg1- and Uhrt-controlled enhancer activation is particularly salient in the disease context, as their dynamic interactions orchestrate different phases of cardiac pathophysiology. The eDNA-Uhrt mode of interaction cautions the use of enhancer transcription as a marker of enhancer activation and emphasizes the importance of studying the transcription of functionally silent enhancers.

What is claimed is:

1. A method of treating a patient at risk for heart disease comprising:
   administering a therapeutically effective amount of an RNA sequence to the patient, wherein the RNA sequence comprises a sequence having at least 95% sequence identity to SEQ ID NO: 2 or its corresponding DNA equivalent thereof.

2. The method of claim 1, wherein the heart disease is hypertrophy.

3. The method of claim 1, further comprising decreasing Brg1 activity.

4. The method of claim 3, wherein the Brg1 activity is decreased by administering an interfering RNA to silence the translation of Brg1.

5. The method of claim 1, further comprising analyzing Uhrt levels after the step of administering the RNA.

6. The method of claim 1, wherein treating the patient comprises inhibiting assembly of a complex of an enhancer DNA (eDNA) with Myh6 promoter-Myh7 promoter in a cardiomyocyte cell by increasing binding of Uhrt to the eDNA, wherein the eDNA comprises a sequence having at least 95% sequence identity with SEQ ID NO: 3.

7. The method of claim 6, wherein the administration increases the concentration of Uhrt RNA and decreases the concentration of eDNA relative to a cell into which the Uhrt RNA and the eDNA was not introduced.

8. The method of claim 1, wherein administering the RNA sequence comprising a sequence having at least 95% sequence identity to SEQ ID NO: 2 or a corresponding DNA equivalent thereof prevents a stress-induced Myh6-to-Myh7 switch.

9. The method of claim 1, wherein the heart disease is heart failure.

10. The method of claim 1, wherein the RNA sequence comprises a sequence having at least 96% sequence identity to SEQ ID NO: 2 or its corresponding DNA equivalent thereof.

11. The method of claim 1, wherein the RNA sequence comprises a sequence having at least 97% sequence identity to SEQ ID NO: 2 or its corresponding DNA equivalent thereof.

12. The method of claim 1, wherein the RNA sequence comprises a sequence having at least 98% sequence identity to SEQ ID NO: 2 or its corresponding DNA equivalent thereof.

13. The method of claim 1, wherein the RNA sequence comprises a sequence having at least 99% sequence identity to SEQ ID NO: 2 or its corresponding DNA equivalent thereof.

14. The method of claim 1, wherein the RNA sequence comprises SEQ ID NO: 2 or its corresponding DNA equivalent thereof.

15. The method of claim 1, wherein the RNA sequence comprises SEQ ID NO: 2.

16. The method of claim 1, wherein the RNA sequence consists of SEQ ID NO: 2.

* * * * *